United States Patent
Badja et al.

(10) Patent No.: US 11,001,803 B2
(45) Date of Patent: May 11, 2021

(54) METHOD FOR GENERATING NEURONAL AND MUSCULAR CELLS

(71) Applicant: ASSOCIATION FRANCAISE CONTRE LES MYOPATHIES, Paris (FR)

(72) Inventors: Cherif Badja, Boumerdes (DZ); Frederique Magdinier, Marseilles (FR)

(73) Assignee: ASSOCIATION FRANCAISE CONTRE LES MYOPATHIES, Paris (FR)

( * ) Notice: Subject to any disclaimer, the term of this patent is extended or adjusted under 35 U.S.C. 154(b) by 986 days.

(21) Appl. No.: 15/500,344

(22) PCT Filed: Jul. 31, 2015

(86) PCT No.: PCT/EP2015/067724
§ 371 (c)(1),
(2) Date: Jan. 30, 2017

(87) PCT Pub. No.: WO2016/016451
PCT Pub. Date: Feb. 4, 2016

(65) Prior Publication Data
US 2017/0226479 A1 Aug. 10, 2017

(30) Foreign Application Priority Data
Jul. 31, 2014 (EP) .................................. 14306229

(51) Int. Cl.
*C12N 5/077* (2010.01)
*C12N 5/074* (2010.01)
*C12N 5/0793* (2010.01)

(52) U.S. Cl.
CPC ......... *C12N 5/0619* (2013.01); *C12N 5/0658* (2013.01); *C12N 5/0696* (2013.01); *C12N 2501/11* (2013.01); *C12N 2501/115* (2013.01); *C12N 2501/119* (2013.01); *C12N 2501/41* (2013.01); *C12N 2501/602* (2013.01); *C12N 2501/603* (2013.01); *C12N 2501/604* (2013.01); *C12N 2501/606* (2013.01); *C12N 2502/081* (2013.01); *C12N 2502/1335* (2013.01); *C12N 2506/1307* (2013.01); *C12N 2506/45* (2013.01); *C12N 2533/52* (2013.01)

(58) Field of Classification Search
None
See application file for complete search history.

(56) References Cited

U.S. PATENT DOCUMENTS

2009/0299763 A1  12/2009  Sakurada

FOREIGN PATENT DOCUMENTS

| EP | 2383333 A1 | 11/2011 |
| WO | WO 01/51616 A2 | 7/2001 |
| WO | 03/020920 A1 | 3/2003 |

OTHER PUBLICATIONS

Hosoyama et al. "Derivation of myogenic progenitors directly from human pluripotent stem cells using a sphere-based culture." Stem Cells Translational Medicine 3.5 (Mar. 21, 2014): 564-574. (Year: 2014).*
Sünwoldt et al. "Neuronal culture microenvironments determine preferences in bioenergetic pathway use." Frontiers in Molecular Neuroscience 10 (2017): 305. (Year: 2017).*
Lan et al. "Myoblast proliferation and differentiation on fibronectin-coated self assembled monolayers presenting different surface chemistries." Biomaterials 26.22 (2005): 4523-4531. (Year: 2005).*
Young et al. "Cryopreservation of embryonic chick myogenic lineage-committed stem cells." Journal of Tissue Culture Methods 13.4 (1991): 275-283. (Year: 1991).*
Yan et al, Efficient and Rapid Derivation of Primitive Neural Stem Cells and Generation of Brain Subtype Neurons from Human Pluripotent Stem Cells, Stem Cells Translational Medicine : SCTM, Alphamed Press, Durham, 2:862-870 (2013).
Matsushita et al., Immediate differentiation of neuronal cells from stem/progenitor-like cells in the avian iris tissues, Experimental Eye Research. vol. 123, Apr. 18, 2014, pp. 16-26.
Silva et al., Neural progenitors from isolated postnatal rat myenteric ganglia: Expansion as neurospheres and differentiation in vitro, Brain Research, Elsevier, Amsterdam, NL, vol. 1218, Jul. 7, 2008, 47-53.
European Patent Office, International Search Report, PCT/EP2015/067724, dated Oct. 9, 2015.
Ramasamy et al., Neural stem cell survival factors, Archives of Biochemistry and Biophysics534 (2013) 71-87.

* cited by examiner

*Primary Examiner* — Emily A Cordas
(74) *Attorney, Agent, or Firm* — Arrigo, Lee, Guttman & Mouta-Bellum LLP

(57) ABSTRACT

The present invention relates to a method for generating neuronal and muscular cells from pluripotent stem cells.

Figure 1:
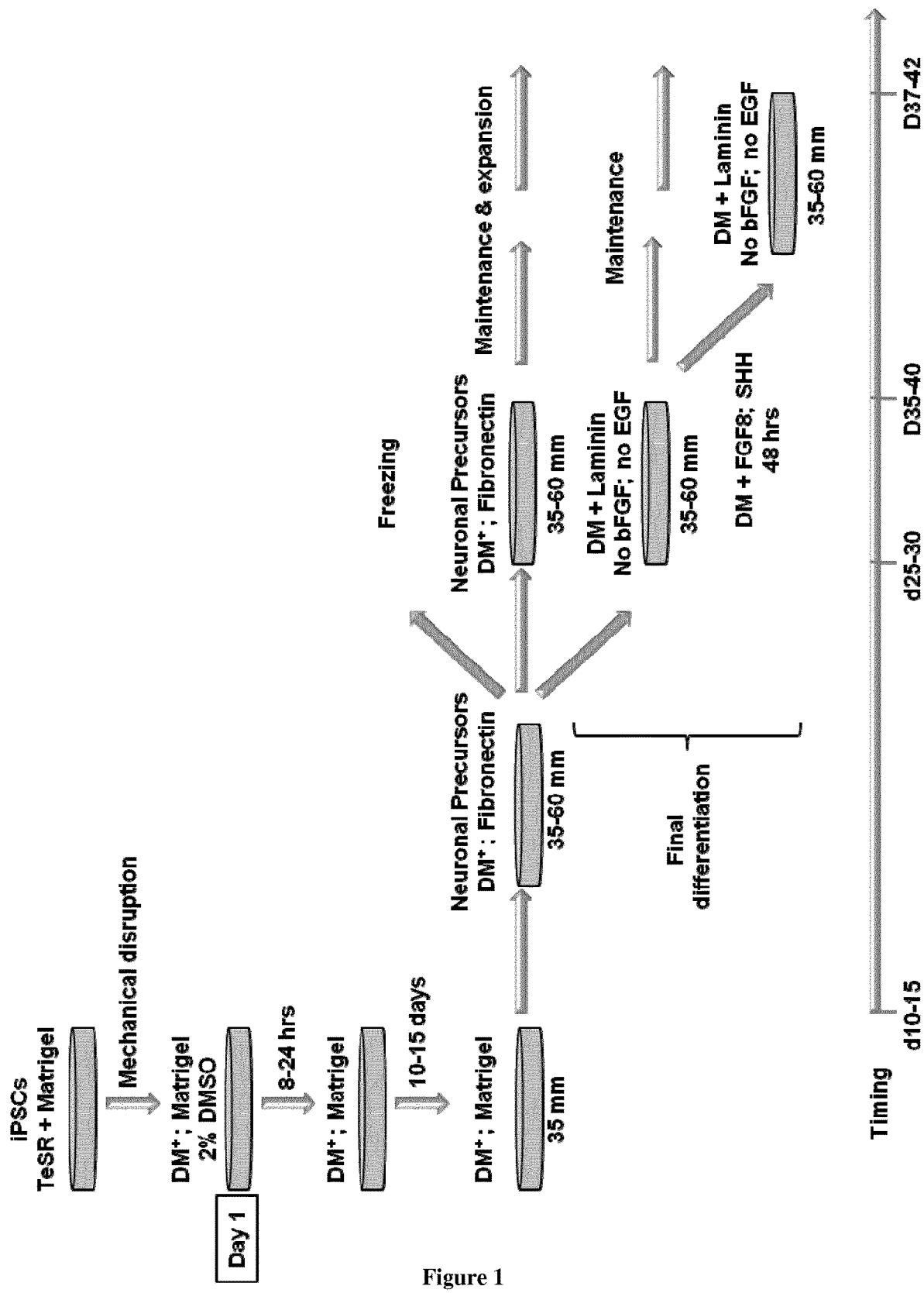

10 Claims, 21 Drawing Sheets
Specification includes a Sequence Listing.

METHOD FOR GENERATING NEURONAL AND MUSCULAR CELLS

FIELD OF THE INVENTION

The present invention relates to a method for generating neuronal and muscular cells from pluripotent stem cells including induced pluripotent stem cells

BACKGROUND OF THE INVENTION

Pluripotent stem cells have the potential to differentiate into almost any cell in the body and are able to self-renew. More recently, the availability of induced pluripotent stem cells (iPSCs), along with their capacity for unlimited proliferation in culture and their potential to differentiate into any different human cell type has provided a potentially invaluable source of materials to improve our understanding of disease pathogenesis, and also for designing and testing new therapeutics, including cell therapy or production of tissues. Indeed, until very recently human disease-specific pluripotent cells could be made only by genetic modification of existing human embryonic stem cells (hESCs) obtained from the inner mass of an embryo after 5-6 days of differentiation or the generation of new hESCs from embryos carrying monogenic diseases detectable via preimplantation genetic diagnosis. These methods are very restrictive, and only a few diseases have been investigated in this way. Thus, the recent development of induced pluripotent stem cells (iPSCs) has brought new promises in the understanding and modeling of a number of human pathologies.

For some lineage commitment, protocols are established but in some cases, experimental development is still required or need to be optimized in order to reduce the cost of the process and obtain large amount of well-characterized differentiated cells.

For example, their is a need to have methods to induce pluripotent stem cells differentiation into bona fide neuronal cells. Such neurons would represent an invaluable tool for the treatment, or as cell models, of central nervous diseases such as Parkinson disease, amyotrophic lateral sclerosis, and Huntington's disease, among many others. Methods for inducing neural derivatives from pluripotent stem cells such as iPSCs are known in the art (e.g. from Yan et al., Stem Cells Transl Med. 2013; 2:862-870) but are not satisfactory yet. Therefore, there is still a need for efficient methods for differentiating pluripotent cells into neuronal cells.

Furthermore, this also holds true for the provision of muscular cells and so far modeling of neuromuscular disorder has been hampered by the absence of efficient protocol for the differentiation of hiPSCs or hESCs into mature skeletal muscle cells. Indeed, while many studies have shown that skeletal muscle cells can be derived from mouse ES or iPSCs cells, only a limited number of studies report an efficient derivation of muscle cells from human ES and iPSCs, in particular due to the paucity of paraxial mesoderm differentiation during embryoid body formation (Darabi et al., Cell stem cell. 2012; 10(5):610-9; Tedesco et al., Sci Transl Med. 2012; 4(140):140ra89; Barberi et al., Nature medicine. 2007; 13(5):642-8; Awaya et al., PLoS One. 2012; 7(12):e51638; Darabi et al., Stem Cells. 2011; 29(5):777-90). Nevertheless, such cells might be useful as well for modeling the large spectrum of pathologies of the muscle including muscular dystrophies but also non-genetically inherited disorders such as muscle wasting associated with ageing, cachexia, atrophy or sarcopenia that affect millions of individuals worldwide or testing new therapeutics such as pharmacological treatment or regenerative cell-based therapies, since no satisfying method for generating such cells from pluripotent cells is available.

SUMMARY OF THE INVENTION

The inventors describe here a novel and efficient method for the differentiation of pluripotent cells into neuronal cells and myotubes. Advantageously, the method requires no feeder layer, even if it can be alternatively applied to pluripotent cells grown on a feeder layer as well. Furthermore, compared to other published protocols, the method of the present invention does not necessitate either embryoid bodies formation for the production of neurons or muscle cells, nor neuronal rosette (primitive neuroepithelial cells) or neurosphere formation (Hitoshi et al., Genes Dev. 2004; 18:1806-1811; Liu et al., Nat Protoc. 2013; 8:1670-1679; Lie et al., Methods Mol Biol. 2012; 873:237-246) for the production of neurons, which might modify the purity of the cell population. The method of the present invention does not require either drug addition, which might perturb the cellular homeostasis (Li et al., Proc Natl Acad Sci USA. 2011; 108:8299-8304; Menendez et al., Proc Natl Acad Sci USA. 2011; 108:19240-19245; Yan et al., Stem Cells Transl Med. 2013; 2:862-870; Chambers et al., Nat Biotechnol. 2009; 27:275-280; Surmacz et al., Stem Cells. 2012; 30:1875-1884), nor cell sorting limiting the quantity of differentiated cells available or ectopic transgene expression (Darabi et al., Cell stem cell. 2012; 10(5):610-9; Tedesco et al., Sci Transl Med. 2012; 4(140):140ra89; Barberi et al., Nature medicine. 2007; 13(5):642-8; Awaya et al., PLoS One. 2012; 7(12):e51638; Darabi et al., Stem Cells. 2011; 29(5):777-90). Moreover, the method of the present invention requires the use of only two cytokines at initial differentiation steps and yields large quantities of neuronal or muscular progenitors in 10-15 days, which can be maintained and regularly expanded or further differentiated. According to previously published protocols, FGF was used for maintaining cells in a undifferentiated state (US 2005/153445) or was first used for growing neural precursors, and then this factor, among others, is proposed to be suppressed to induce cell differentiation (US 2002/090723). However, the prior protocols do not suggest that EGF might be an important factor for inducing and growing pluripotent cells to the neuronal lineage and that suppressing EGF together with FGF from the culture medium would be advantageous in further differentiating these cells into neurons or myotubes. Furthermore, one skilled in the art would expect that such protocols would be improved by using BDNF and GDNF such as provided by Yan et al., 2013 (supra), rather by culturing the cells in EGF and then withdrawing this factor from the culture medium.

Accordingly, the invention provides a method for generating neurons or myotubes, comprising the steps of:

a) providing cells induced into the neuronal or muscular lineage from pluripotent stem cells and maintained in a culture medium comprising a member of the FGF family of proteins and EGF on a support coated with fibronectin; and b) culturing said induced cells in a culture medium devoid of any member of the FGF family of proteins and of EGF either on a support coated with laminin for obtaining neurons or on a support coated with fibronectin for obtaining myotubes or a mixture of myotubes and neurons.

In an embodiment, the cells of the neuronal or muscular lineage used in step b) are obtainable by:

i. culturing pluripotent stem cells in a medium containing bFGF, EGF and DMSO; then ii. culturing the cells in a medium containing bFGF and EGF and devoid of DMSO; and then iii. culturing the cells in a medium containing bFGF and EGF and devoid of DMSO on a support coated with fibronectin.

The present invention also relates to a cell of the neuronal or muscular lineage (or also termed a neuronal or muscular progenitor) obtainable according to step i to iii as defined above.

In another embodiment, the duration of the culturing step i) is between 8 and 24 hours, the duration being in particular of 16 hours. In a further embodiment, the duration of the culturing step ii) is between 4 and 20 days, in particular between 10 and 20 days, the duration being more particularly of 15 days in order to reach an enrichment of at least 90% of the desired cell lineage. In another embodiment, the duration of step iii) is of at least 5 days, more particularly of at least 10 days. According to a further embodiment, the duration of step b) is of at least 3 days.

Advantageously, the cells may be frozen or expanded between steps a) and b).

In another embodiment, a further step of terminal differentiation into specialized neurons, such as dopaminergic neurons, is implemented after step b). In particular, dopaminergic neurons may be obtained by culturing the cells obtained after step b) in a medium containing FGF8 and SHH for example for a duration of 48 hours. Differentiation towards the production of GABAergic neurons may be obtained in the presence of SHH, differentiation towards the production of Glutamatergic neurons may be obtained in the presence of Retinoic acid, and differentiation towards the production of motoneurons may be obtained in the presence of SAG (Smoothened Agonist), Retinoic Acid and CHIR 99021 (6-[[2-[[4-(2,4-dichlorophenyl)-5-(5-methyl-1H-imidazol-2-yl)-2-pyrimidinyl]amino]ethyl]amino]-3-pyridinecarbonitrile).

The method of the invention allows generating, using simple and robust conditions, large populations of neurons and myotubes. Such cells may be employed in various applications such as pharmacological, toxicological or genetic screening assays, in cellular models of normal brain or muscle development and function, as well as of neurological, neuropsychiatric, neuromuscular or muscular diseases, and in neuron- or muscle-replacement therapies of such diseases.

These and further aspects and preferred embodiments of the invention are described in the following parts.

LEGEND OF THE FIGURES

FIG. 1: a diagram showing a representative embodiment of the method according to the invention for producing neurons.

Days 1-15; differentiation of hiPSCs into human neuronal stem cells (hNSCs). hiPSCs are expanded and mature hiPSCs cultured in mTeSR on MATRIGEL-coated plates are mechanically disrupted in 30 to 50 small clumps using a 23G needle and plated onto a MATRIGEL-coated 35 mm culture dish in Differentiation Medium (DM) supplemented with 20 ng/ml bFGF, 20 ng/ml EGF (DM+). Optimal results were obtained with 2% (v/v) DMSO for 16 hrs. After an overnight incubation, medium is replaced with DM+. Differentiated cells progressively emerge as a monolayer in the periphery of the hiPSC colony and can be maintained and expanded for up to 15 days with medium replacement every day. After 10-15 days of differentiation, cells at a 90-100% confluency are dissociated with Dispase. Small clumps of hNSCs are plated onto Fibronectin-coated 35 mm culture dishes and 90% of cells adhere within a few minutes after plating. hNSCs can be maintained for several passages or expanded after splitting with ACCUTASE or a cell scraper and replating at a density of $1 \times 10^5$ cell/35 mm culture dish. For final differentiation, cells are mechanically separated with a 23G needle and plated onto Laminin-coated 6 well plates in DM without bFGF and EGF. Medium is replaced every day.

Neurons develop in 5 to 7 days after plating. An example of final differentiation into dopaminergic neurons is presented after addition of specific cytokines, such as FGF8 and SHH.

Figure 2:
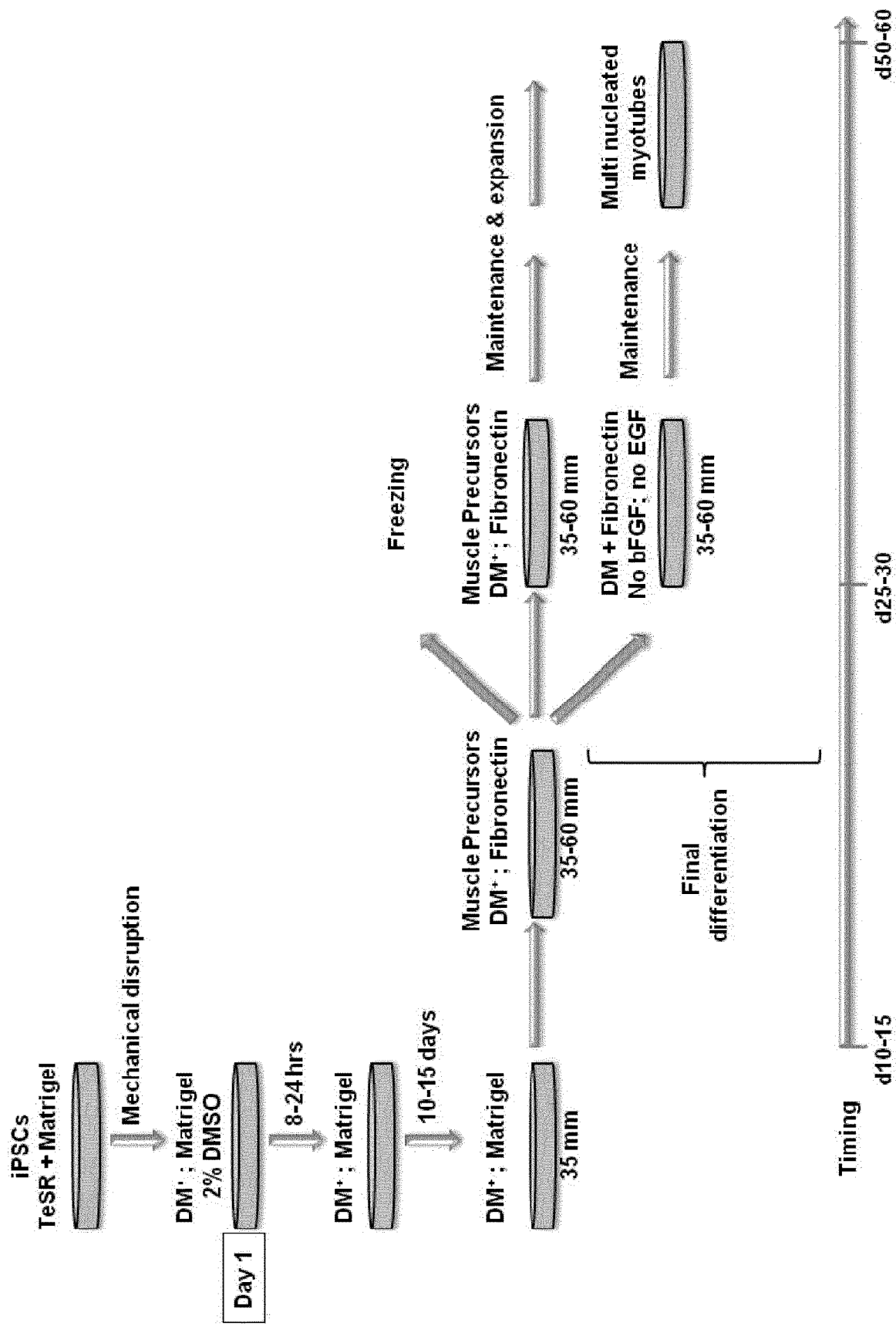

FIG. 2: is a diagram showing a representative embodiment of the method according to the invention for producing myotubes.

Days 1-15; differentiation of hiPSCs into human muscle progenitors. hiPSCs are expanded and mature hiPSCs cultured in mTeSR on MATRIGEL-coated plates are mechanically disrupted in 30 to 50 small clumps using a 23G needle and plated onto a MATRIGEL-coated 35 mm culture dish in Differentiation Medium (DM) supplemented with 20 ng/ml bFGF, 20 ng/ml EGF (DM+). Optimal differentiation was obtained with incubation in the presence of 2% (v/v) DMSO for 16 hrs. After this overnight incubation, medium is replaced with DM+. Differentiated cells form large aggregates that can be mechanically separated and dissociated. Small clumps of cells are plated onto Fibronectin-coated 35 mm culture dishes and 90% of cells adhere within a few minutes after plating. These muscle precursors can be maintained for several passages or expanded. For final differentiation, cells are mechanically separated with a 23G needle and plated onto Fibronectin-coated 6 well plates in DM without bFGF and EGF. Medium is replaced every day. Muscle cells develop in 5 to 7 days after plating and start to fuse and form elongated multinucleated myotubes in 10-15 days.

Figure 3:
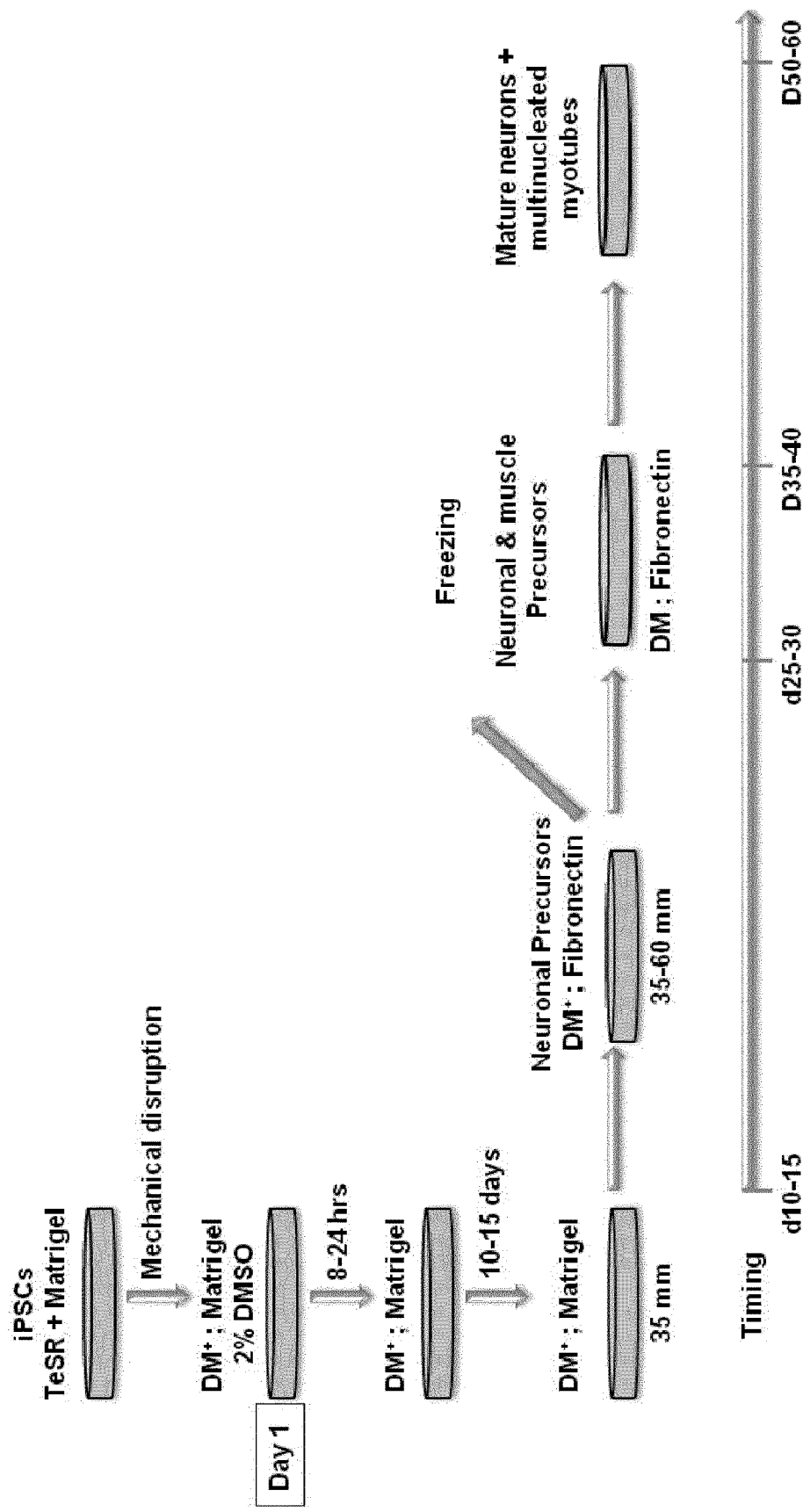

FIG. 3: is a diagram representing a representative embodiment of the method according to the invention for producing neurons and myotubes.

Days 1-15; Mature hiPSCs are expanded in mTeSR on MATRIGEL-coated plates and mechanically disrupted in 30 to 50 small clumps using a 23G needle. For differentiation, cells are plated onto a MATRIGEL-coated 35 mm culture dish in Differentiation Medium (DM) supplemented with 20 ng/ml bFGF, 20 ng/ml EGF (DM+) and 2% (v/v) DMSO for 16 hrs. After an overnight incubation, medium is replaced with DM+. Differentiated cells progressively emerge as a monolayer in the periphery of the hiPSC colony and can be maintained and expanded for up to 15 days with medium replacement every day. After 10-15 days, cells reach a 90-100% confluency. For final differentiation and co-culture of neurons and muscle cells, cells grown either as a monolayer or cell aggregates grown in suspension are scraped for example using a cell scraper or a 23G needle, collected, mechanically dissociated and aliquots are plated onto fibronectin-coated 6-well plates in DM without bFGF and EGF. Medium is replaced every day.

Figure 4:
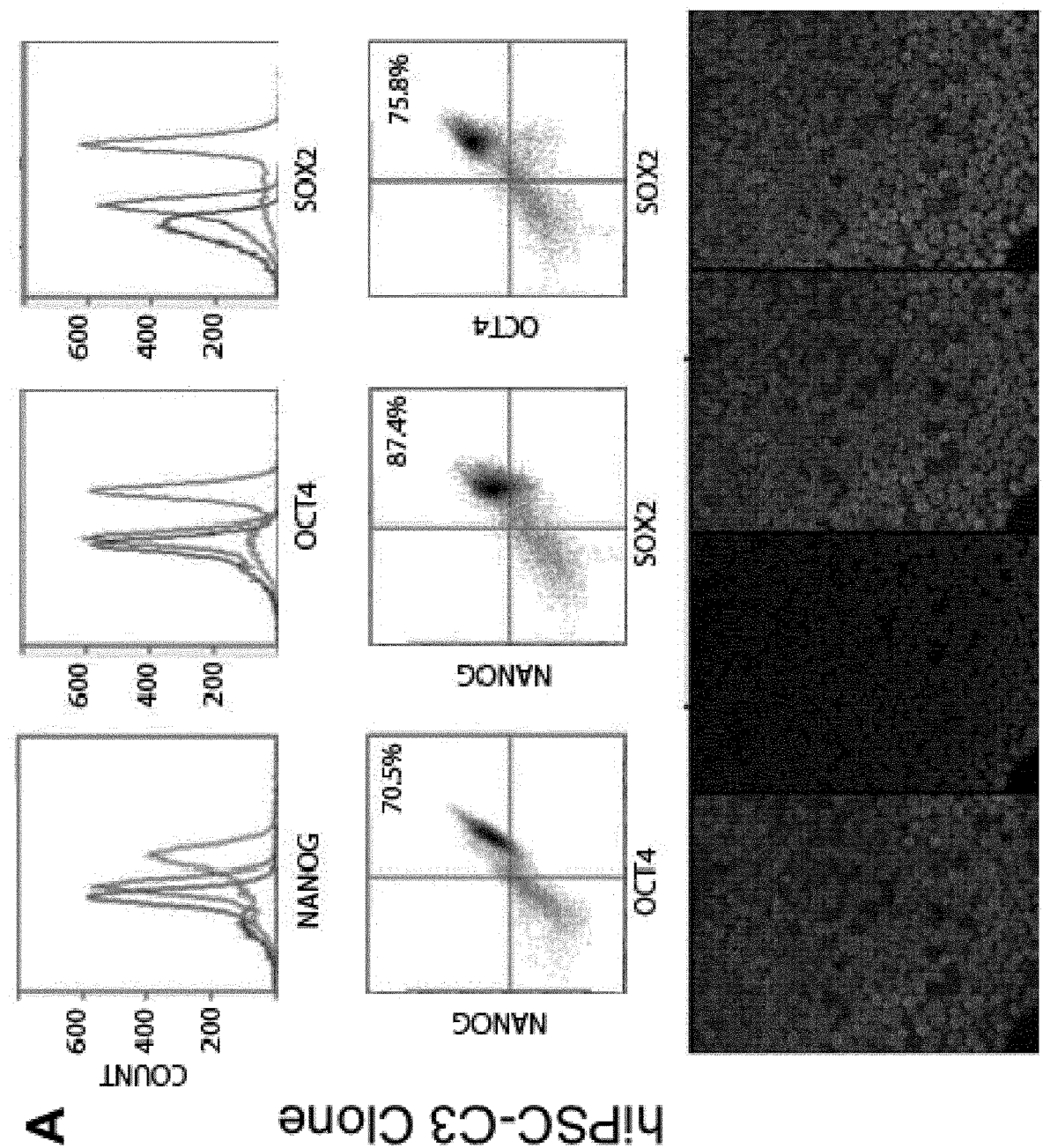
Figure 4:
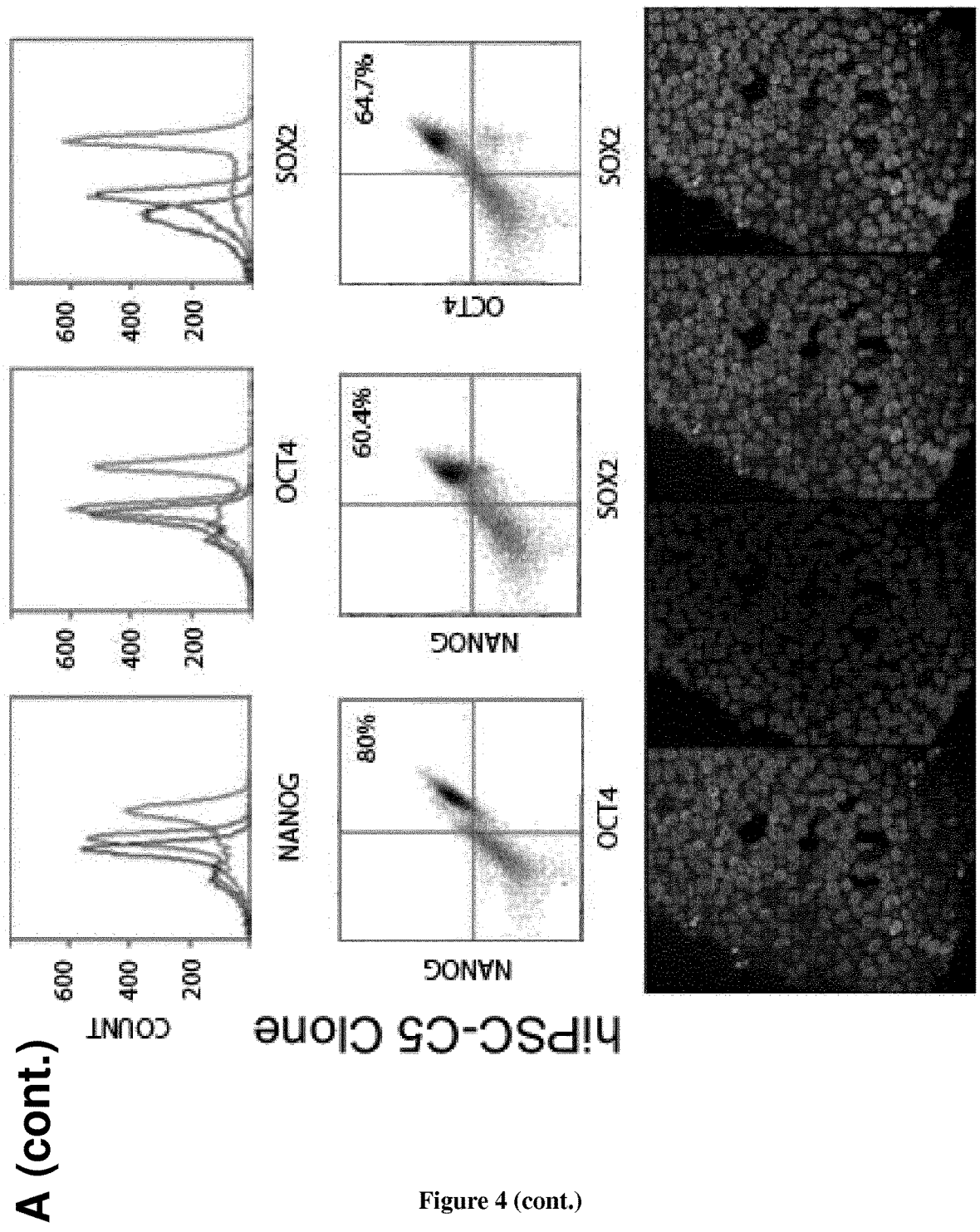
Figure 4:
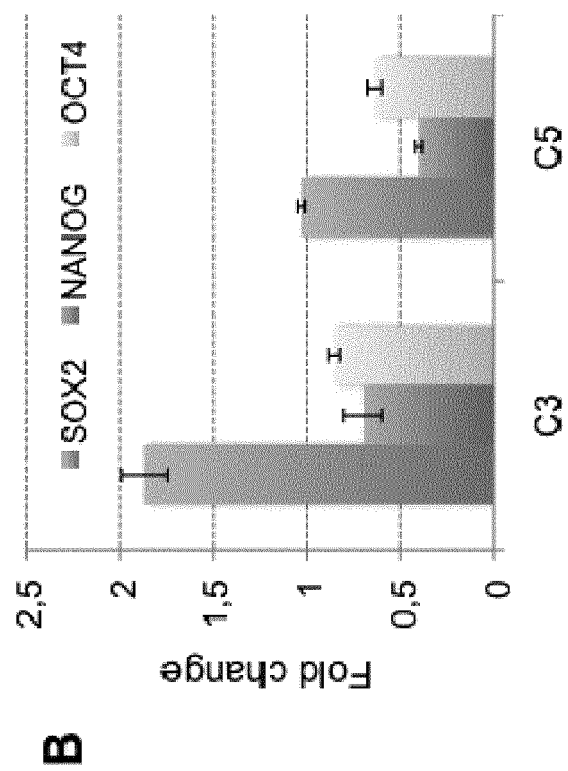
Figure 4:
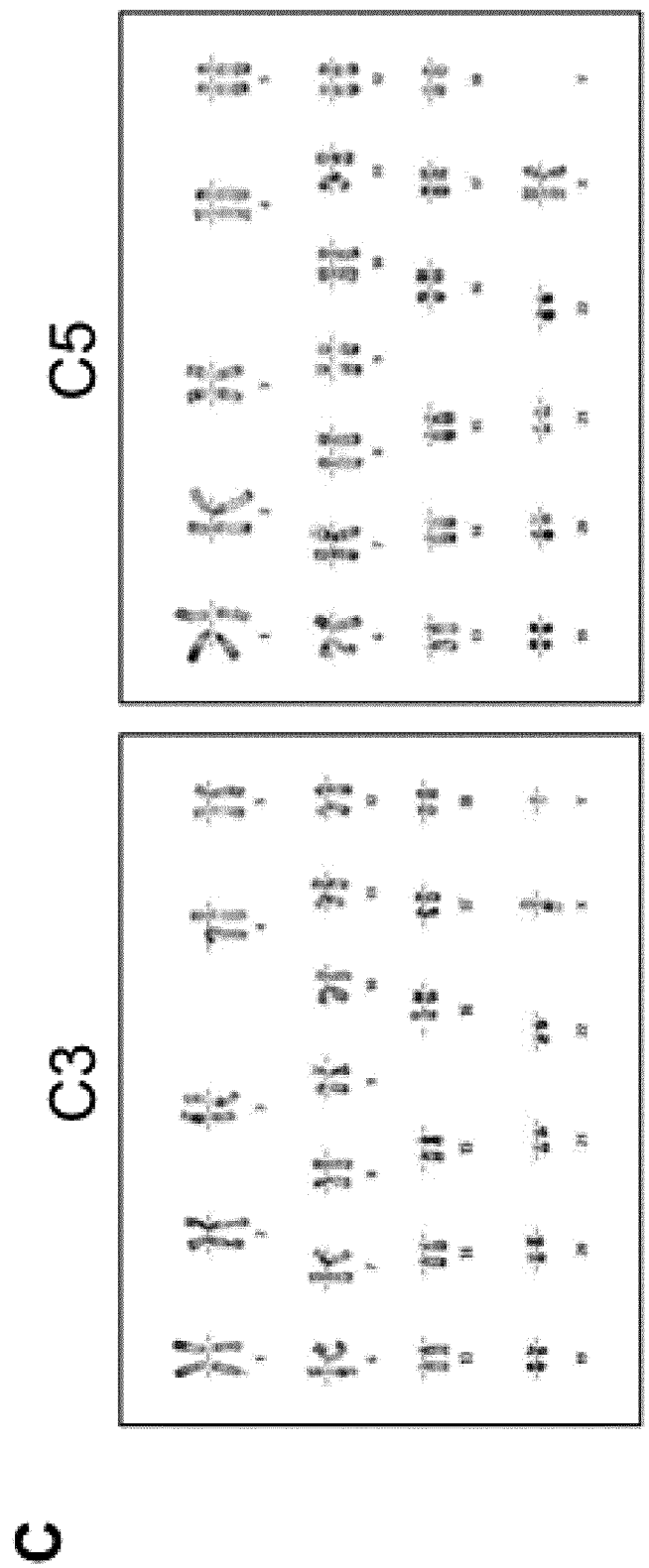

FIG. 4: characterization of hiPSCs. Human induced pluripotent cells were independently established in our laboratory by lentiviral infection of two different primary fibroblast cell lines with a polycistronic vector expressing OCT4, KLF4, SOX2 and c-MYC (OKSM vector, Millipore). C3 was derived from a commercial human foreskin fibroblast line (Millipore). The C5 clone was derived from primary fibroblasts (Ref AG08498) obtained from the Coriell. Data presented were obtained from clones C3 and C5 but other clones were also tested (data not shown). These hiPSCs showed human ES-like morphology and express the SOX2, OCT4 and NANOG stem cell markers as determined by flow cytometry analysis (A, upper panels) and immunofluorescence (A, lower panels) or quantitative RT PCR (B) and did not display any karyotype defect (C). In addition, these cells are able to differentiate and form embryoid bodies when grown in suspension (data not shown).

Figure 5:
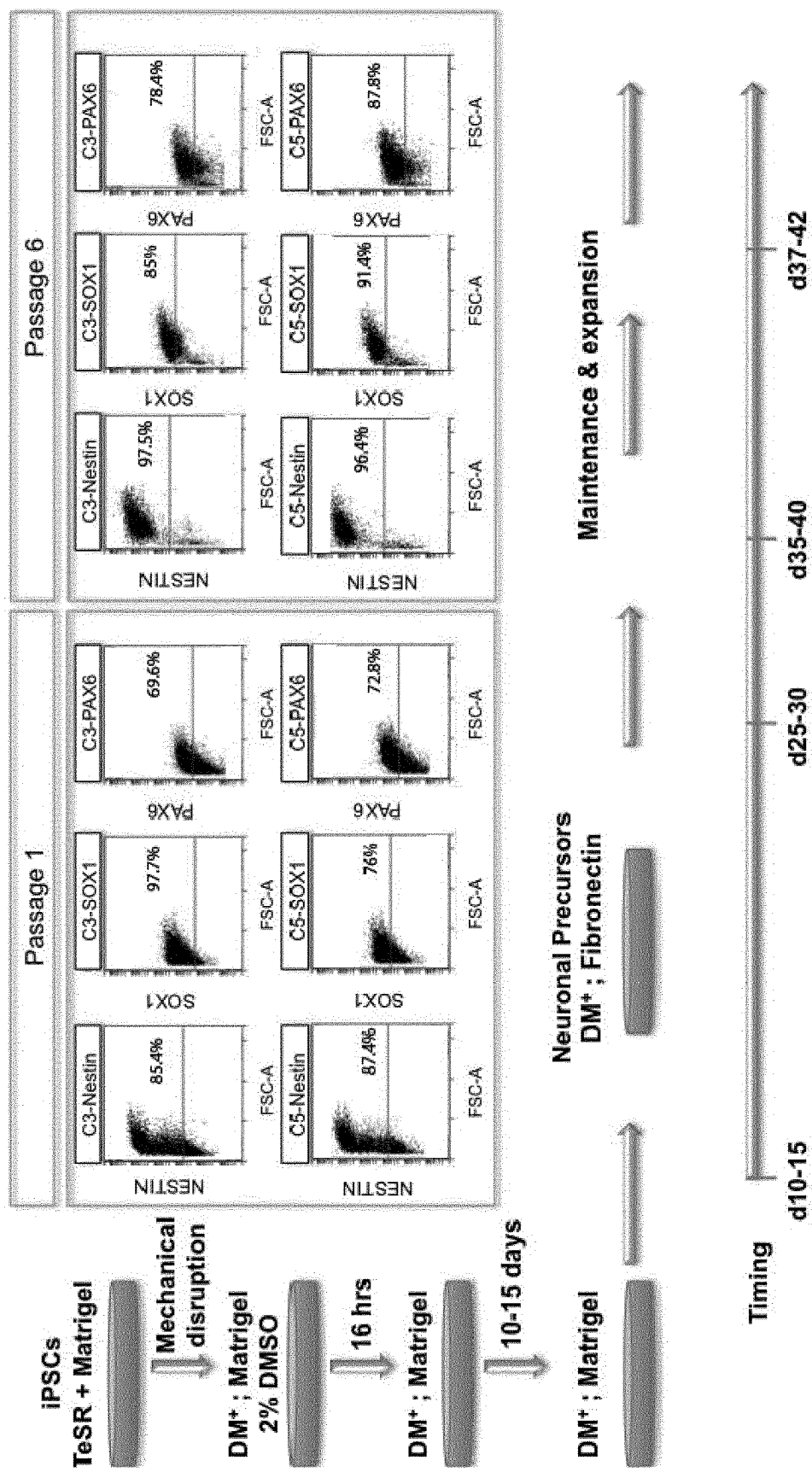

FIG. 5: procedure for production and expansion of neuronal progenitors. After induction of the differentiation process, colonies are picked between days 10 and 15 and cultured in a defined medium on Fibronectin. At this step, cells can also be frozen without loss of differentiation potential as indicated by flow cytometry analysis with different markers expressed in neuronal progenitors. FACS was performed after the first or the 6th passage. Representative results obtained from two clones (C3 and C5 are presented). Isotype-specific control antibodies were used as controls.

Figure 6:
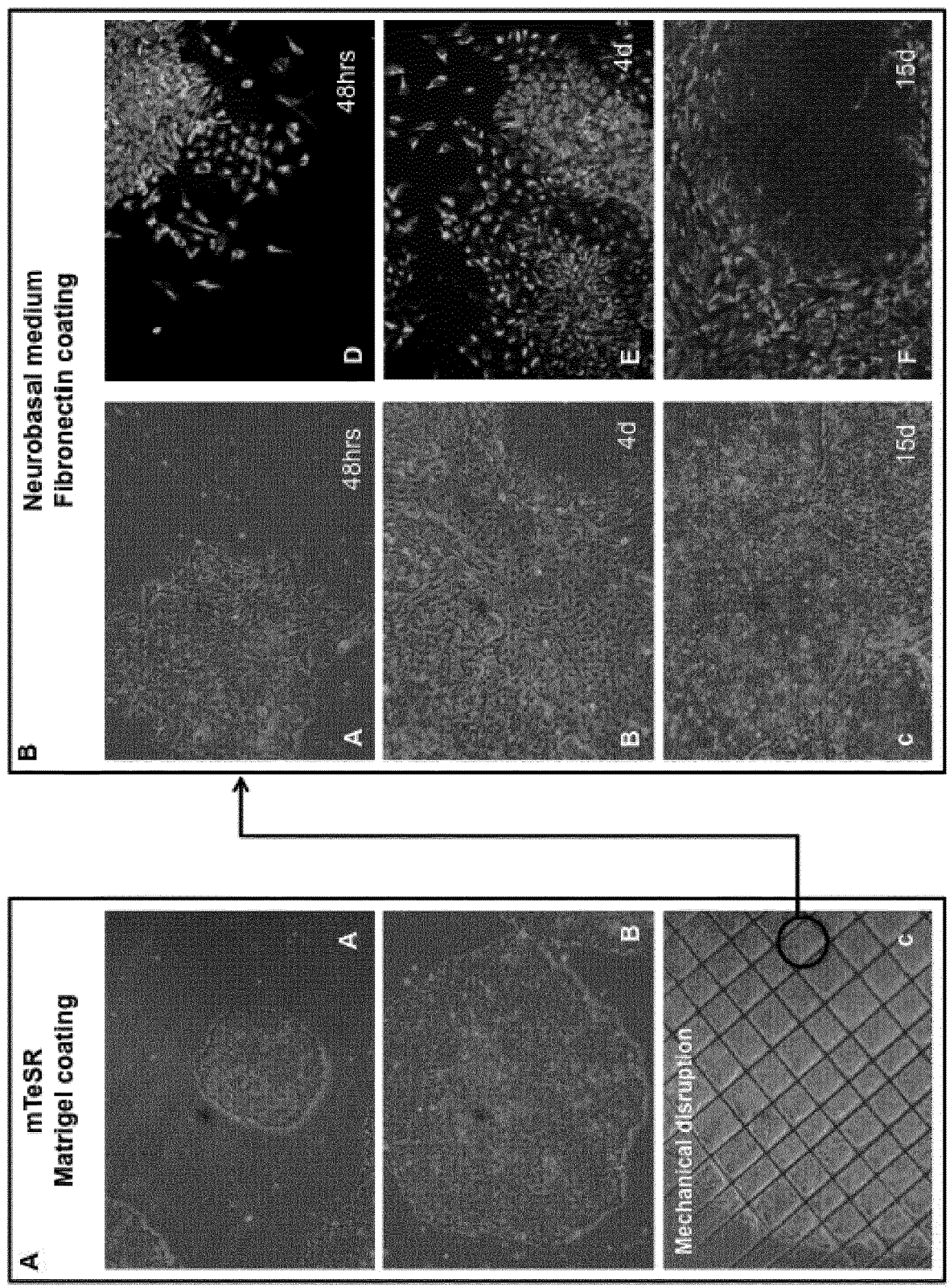

FIG. 6: Differentiation of hiPSCs into neuronal progenitors.

A. Bright field images of a small immature (a) and mature (b) hiPSC colony grown on MATRIGEL-coated plates in mTeSR before mechanical disruption (c). B. After mechanical disruption using a 23G needle, clumps of cells are plated on MATRIGEL and grown in differentiation medium. Left, bright field images of neuronal differentiation 48 hours (a); 4 days (b) or 15 days (c) post induction. (d) 48 hours post-induction, differentiated cells expressing the Nestin neuronal marker (green) migrate out of the OCT4-positive hiPSC colony (red). (e), neuronal precursors expressing Nestin (green) and hiPSC expressing OCT4 at day 4 post-induction. After 15 days (f), OCT4 expression is barely detectable and Nestin-positive neuronal precursors reach a 90-100% confluency.

Figure 7:
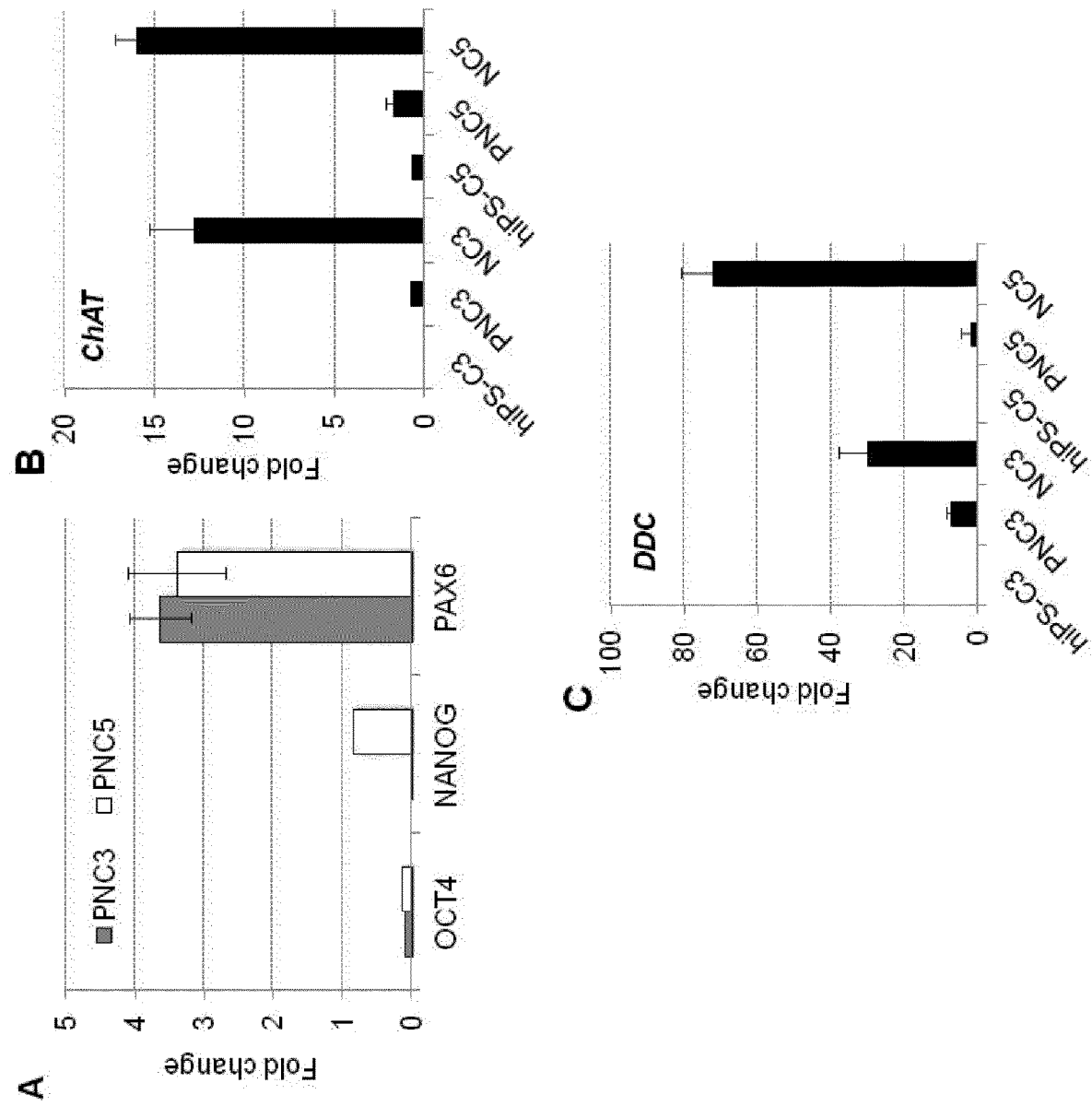

FIG. 7: Expression of neuronal markers.

A. Expression of neuronal progenitors markers was determined by quantitative RT-PCR (PAX6) in hiPSCs cells from clones 3 and 5 (hiPS-C3 and hiPS-05 respectively) and neuronal progenitors at day 20 post-induction (PNC3 and PNCS).

B. Expression of the ChAT (choline acetyltransferase) markers of mature neurons was determined by RT-QPCR in hiPSCs cells from clones 3 and 5 (hiPS-C3 and hiPS-05 respectively), neuronal progenitors at day 30 post-induction (PNC3 and PNCS) or mature neurons (NC3 and NC5) 15 days after plating of neuronal progenitors on Laminin coated dishes.

C. Expression of the dopaminergic neuron markers DDC (encoding DOPA decarboxylase) was evaluated in dopaminergic neurons, 15 days after induction in the presence of SHH and FGF8.

Figure 8:
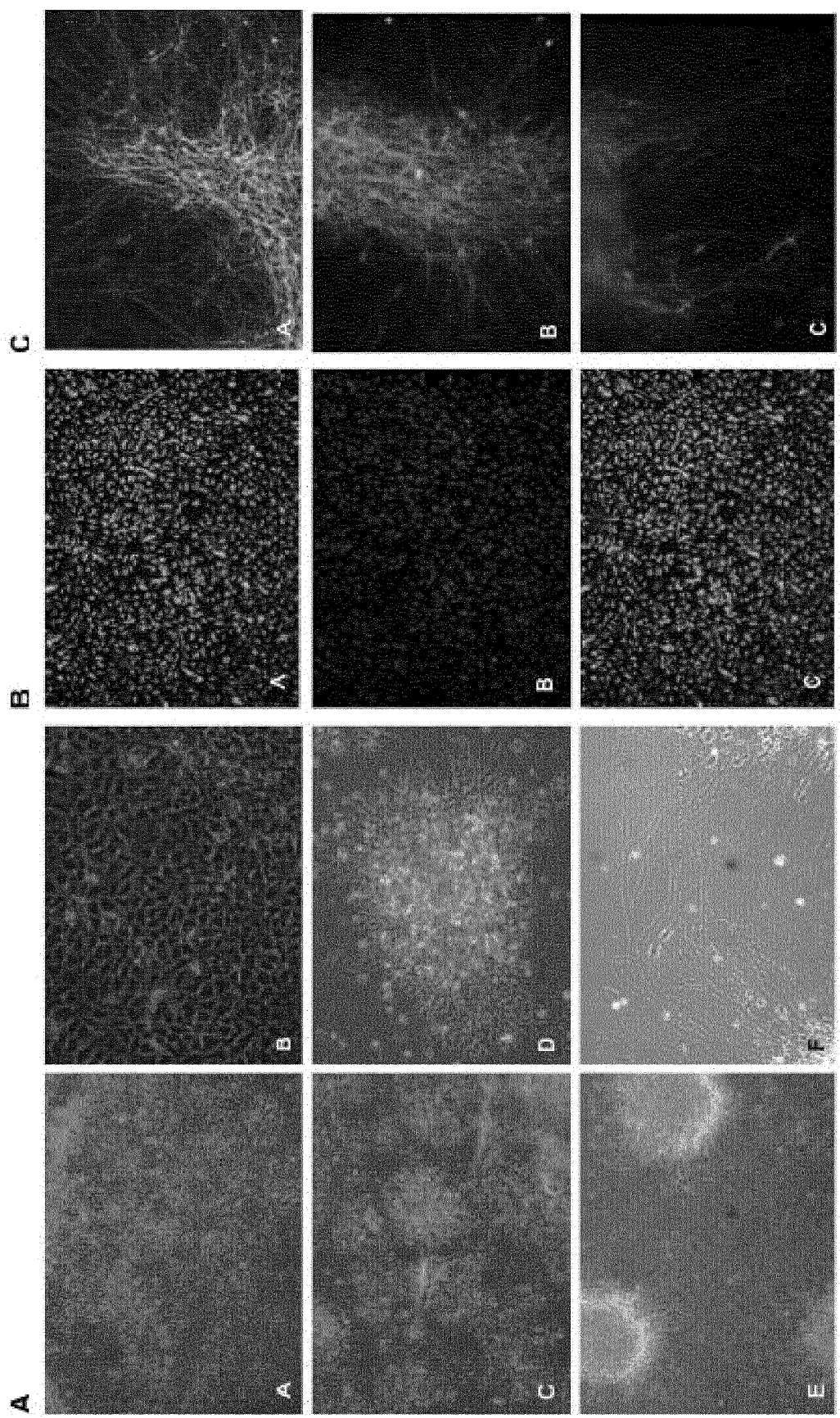

FIG. 8: Production of mature neurons.

A. Illustration of the different steps of neuronal maturation. Neuronal progenitor can be expanded on solid-coated plates to a 90-100% confluency ((a) ×5 magnification; (b), ×10 magnification) or dissociated and plated at a lower density ((c) ×5 magnification; (d), ×10 magnification) for further differentiation ((e) ×5 magnification; (f), ×10 magnification).

B. Immunofluoresence staining two days after plating of neuronal progenitors on Laminin in NB but without bFGF and EGF. The majority of cells express Nestin (a); cells were counterstained with DAPI (b); (c) merge.

C. In 20-30 days, mature neurons derived from hiPSCs express βIII Tubulin (panels a,b) and the marker of mature neurons, NeuN (b). Dopaminergic differentiation was induced by addition of SHH and FGF8 as described. The production and functionality of Dopaminergic neurons was assessed by immunofluorescence staining with antibodies against Tyrosine Hydroxylase 15 days after induction (c).

Figure 9:
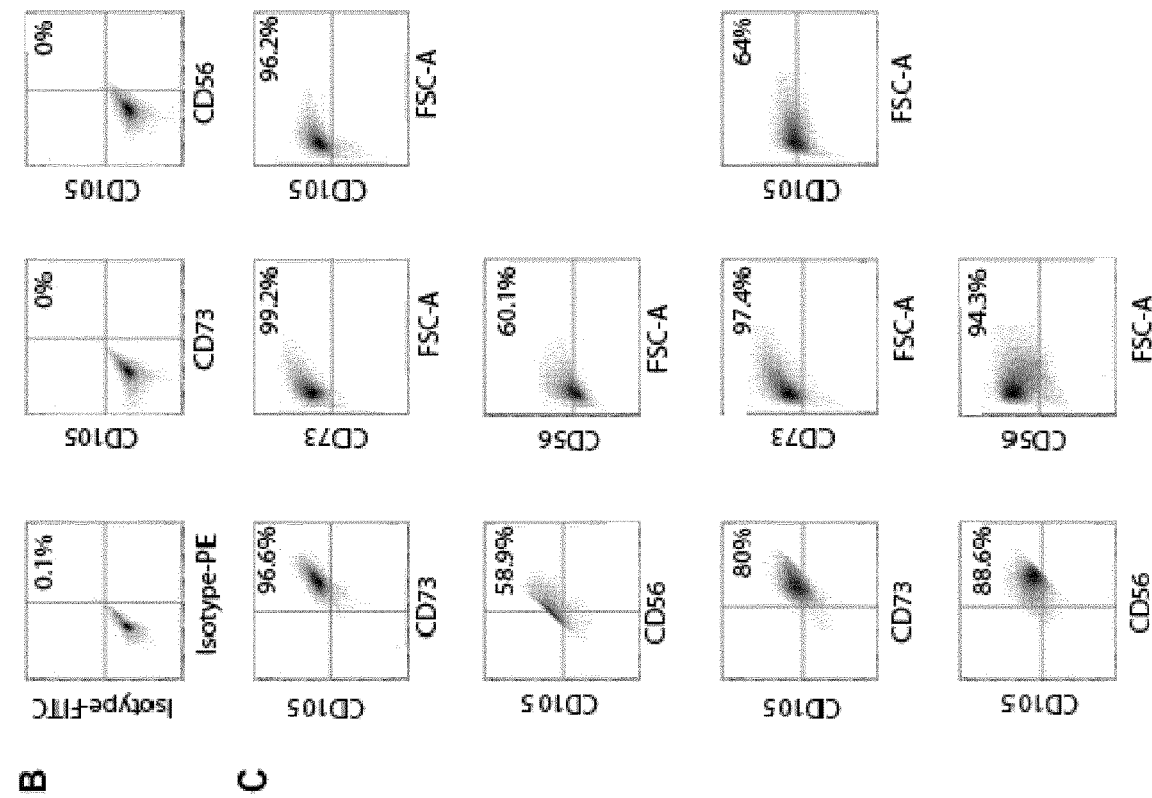
Figure 9:
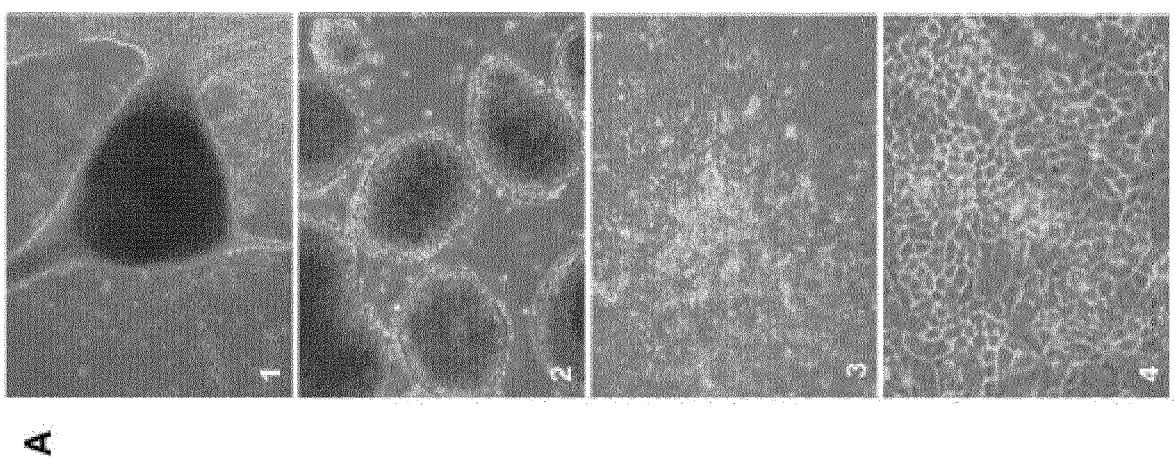

FIG. 9: Myogenic progression requires passage through a transient mesenchymal stage.

Panel A illustrates the different steps of skeletal muscle differentiation. (1) cell aggregates; (2) small clumps obtained after mechanical disruption of cell aggregates; (3) formation of a monolayer of mesenchymal progenitors (×10); (4) ×20. B. Mesenchymal progenitors were characterized by flow cytometry with antibodies against the CD105 and CD73 mesenchymal stem cell markers and CD56, a marker of muscle cell commitment. Non-induced hiPSCs were used to determine the baseline. C. The percentage of mesenchymal stem cells positive for CD73 and CD105 and committed muscle cells positive for CD56 was determined by flow cytometry. Isotypes were used to determine the background of fluorescence and compensation was determined for individual fluorochromes. Forward Scatter (FSC-A).

Figure 10:
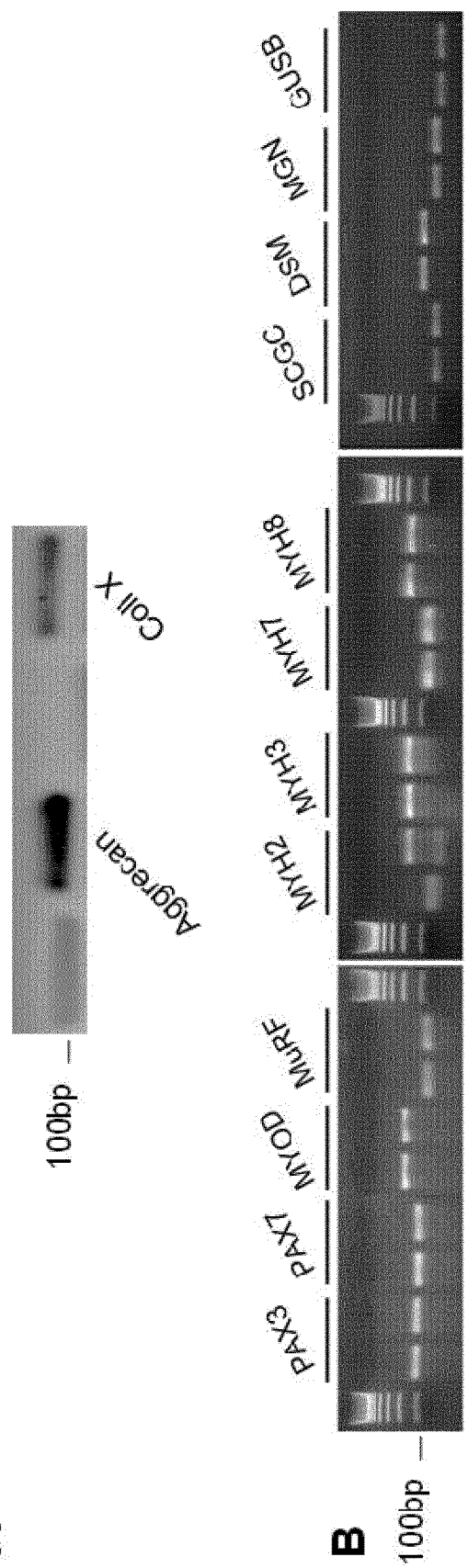

FIG. 10: Characterization of hiPSCs-derived muscle cells.

A. In order to determine whether mesenchymal stem cells isolated at early differentiation stages are already committed toward the muscle cell lineage or still competent for mesenchymal differentiation, we tested the ability of these cells to form micropellet expressing Aggrecan and Collagen X when grown in suspension in the presence of BMP2.

B. Expression of genes expressed during skeletal myogenesis such as PAX3, PAX7, MURF1, MYOD or Myogenin (MGN) was monitored by RT-PCR together with expression of Class II Myosin heavy chain genes (MYH2, MYH3, MYH7, MYH8), Sarcoglycan (SCG) and Desmin (DSM)

Figure 11:
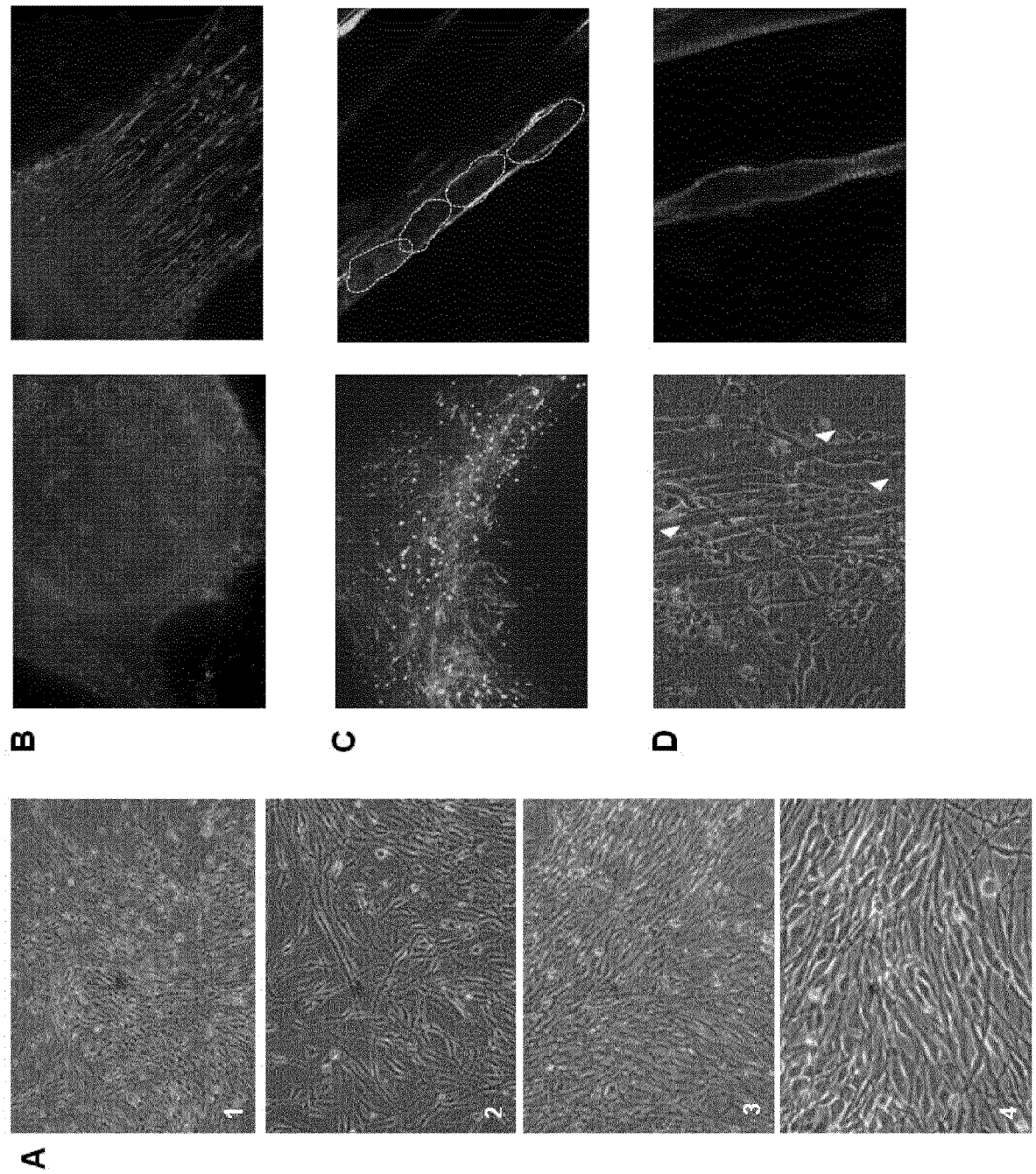

FIG. 11: Formation of elongated multinucleated muscle fibers with Z-line like sarcomeric organization.

A. Representative phase contrast micrographs showing the formation of muscle fibers (1-3; ×10 magnification; 4, ×20). B. Immunochemistry of hiPSCs-dervived muscle cells (1) MYOD; (2) DESMIN. C. (1) MF20; (2) MYOD-positive nuclei delimitated by a white dotted line in a MF20-positive fiber. D. Illustration of the sarcomeric organization that takes place at late differentiation stage (picture 1, white arrows indicate the striations) in Myosin Heavy chain-positive multinucleated fibers derived from hiPSCs. In photograph 2, nuclei are stained with MYOD and myotube is stained with antibody against sarcomeric myosin heavy Chain (MF20).

Figure 12:
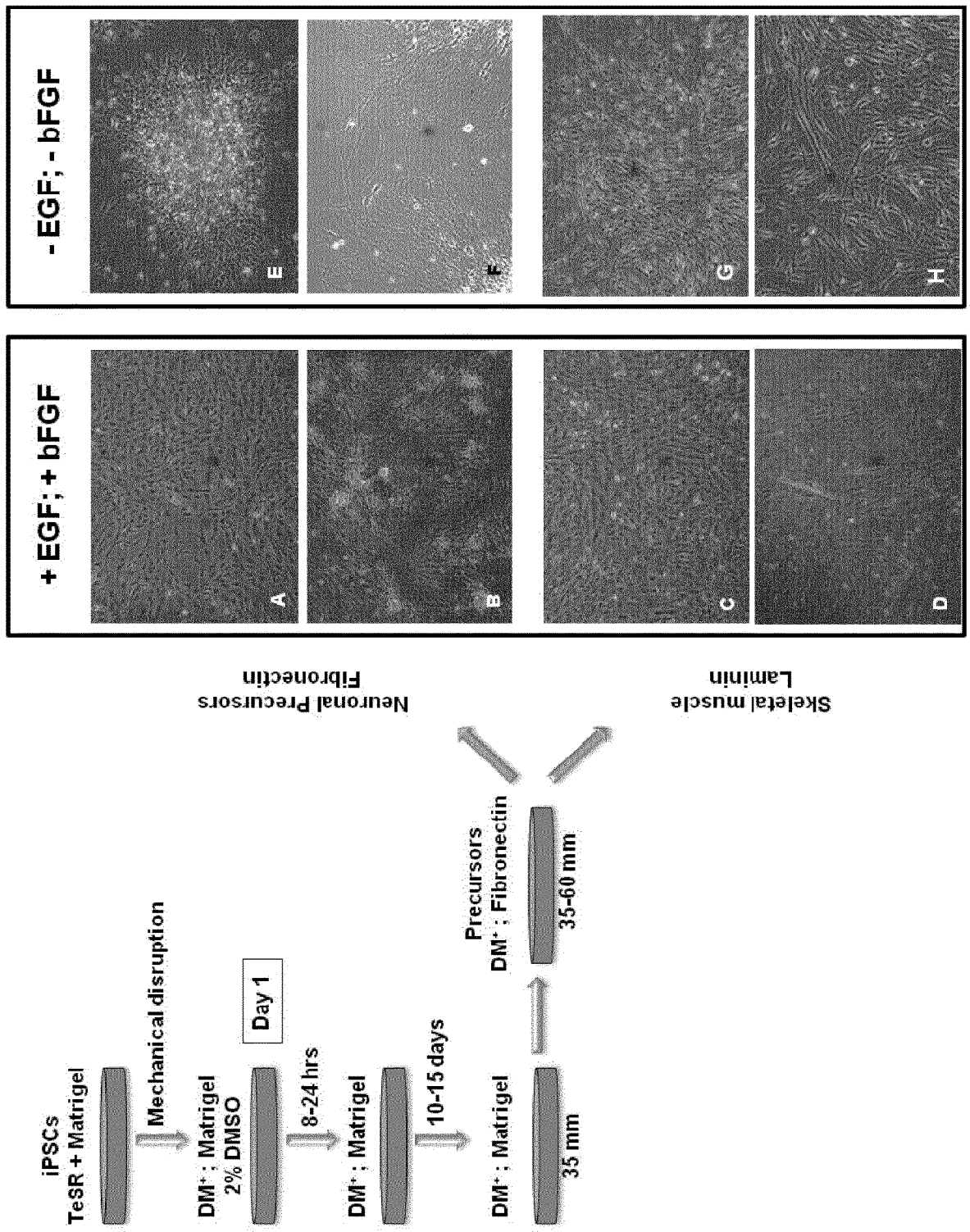

FIG. 12: Final neuronal or skeletal muscle differentiation is impeded by the presence of FGF and EGF. Final differentiation toward the neuronal (A) and (E) or muscle lineage (C) and (G) was tested in the presence (A) and (C) or absence (E) and (G) of EGF (20 ng/ml) and bFGF (20 ng/ml). After plating on Laminin for neuronal differentiation (A) or fibronectin for skeletal muscle (C) cells were maintained for 20-30 days. Cell morphology, enrichment in mature neurons (B) or multinucleated myotubes (D) were compared to conditions where the two cytokines are omitted (Panel F and H, respectively).

Figure 13:
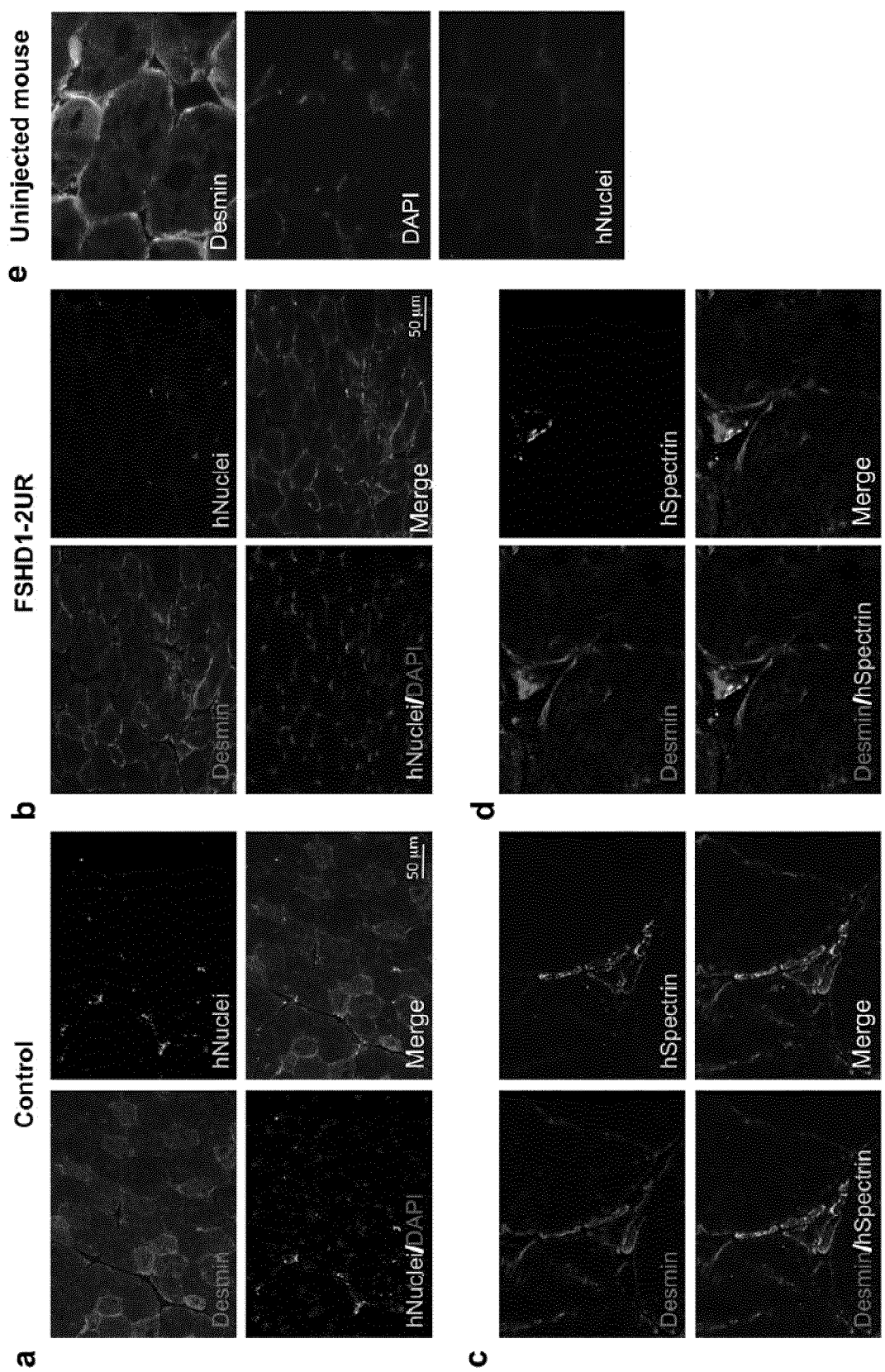

FIG. 13: Long term engraftment and regenerative capacity of control and hiPSCs-derived skeletal muscle progenitors.

Representative immunostaining of TA cross-sections of NOD/SCID mice injected with $5 \times 10^5$ hiPSCs-derived muscle progenitors at day 20 of differentiation. a-b. Thirty days post-engraftment, grafted cells were identified by using the human nuclear antigen marker. Fibers were counterstained with Desmin which stains both human and mouse muscle. Nuclei were counterstained with DAPI. c. d. Muscle injected with control or hiPSCs-derived cells positively stained for human spectrin. Fibers were stained with Desmin which stains both human and mouse muscle and nuclei were counterstained with DAPI. e. Uninjected TA was stained with antibodies against Desmin (upper panel) or anti-human Nuclei antigen (lower panel) in order to verify that the antibody was specific to human cells.

Figure 14:
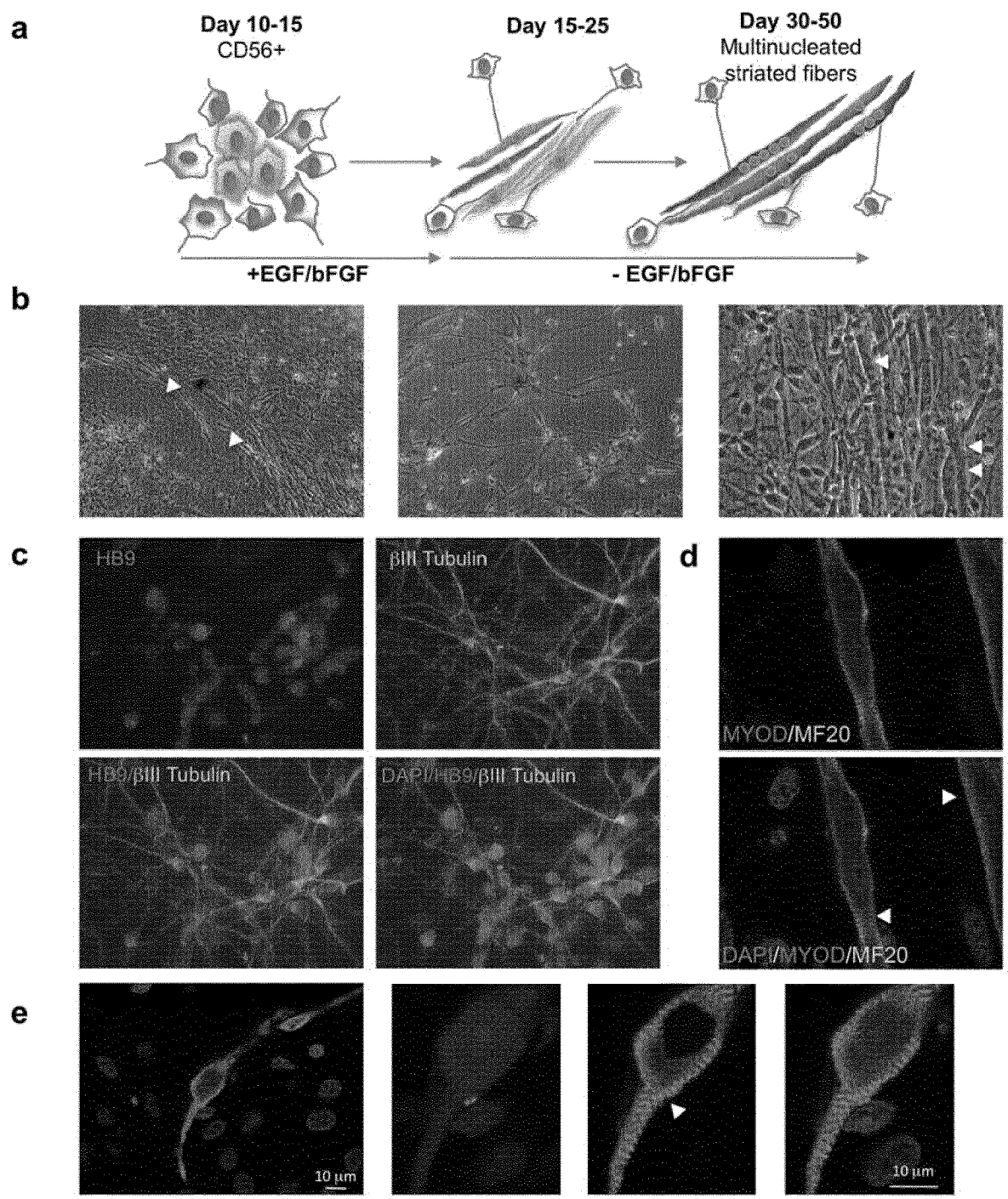

FIG. 14: In the presence of hiPSCs-derived motoneurones, elongated multinucleated muscle fibers form Z-line sarcomeric structures and neuromuscular junctions.
a. Schematic representation of the procedure used for co-differentiation of neuronal and muscle progenitors on fibronectin-coated plates. Neuronal and muscle precursors were plated on fibronectin in a 2:1 ratio and cultured in differentiation medium without mitogens and maintained for 20-30 days. b. Bright field images of the different populations of cells, left, oriented muscle fibers surrounded by neurons (indicated by arrows); middle, higher magnification; right, Illustration of the sarcomeric organization that takes place at late differentiation stage (arrows indicate the striations). c. Representative images of immunostaining of motor neurons obtained in muscle-neurons cocultures. HB9 or b-Tubulin staining and overlays. d. Expression of Myosin Heavy Chain and MYOD in multinucleated fibers forming Z line-like structure. Striations are indicated by arrows. Nuclei are counterstained with DAPI. e. Myotubes are stained with MF20. Acetylcholine receptor clustering is visible at the surface of myotubes after staining with α bungarotoxin coupled with ALEXA FLUOR 555 at ×63 magnification. Nuclei are counterstained with DAPI.

Figure 15:
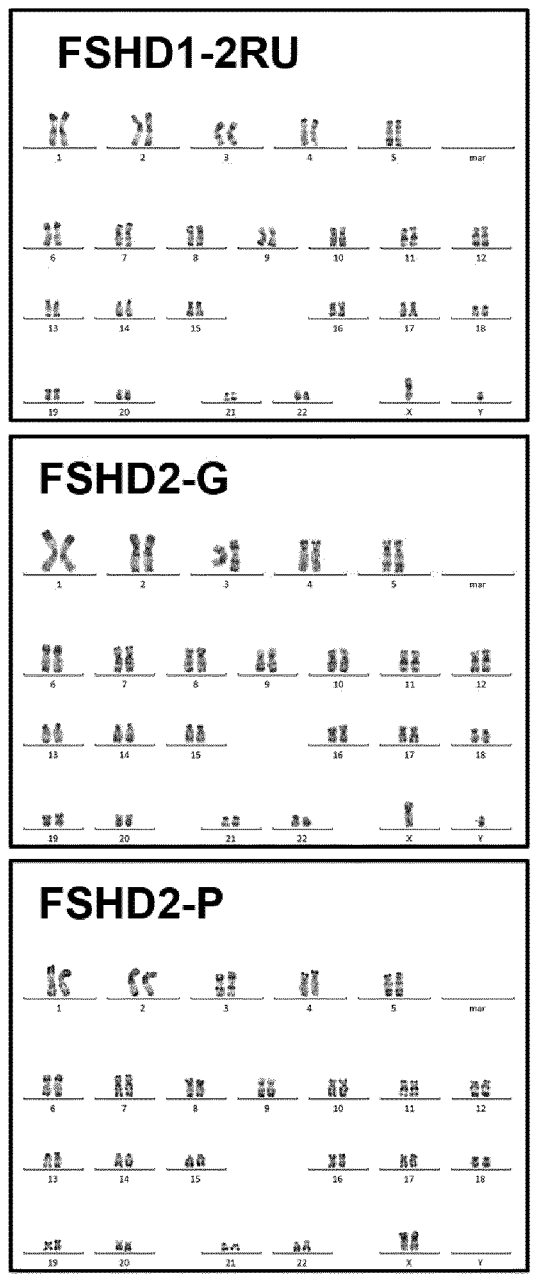
Figure 15:
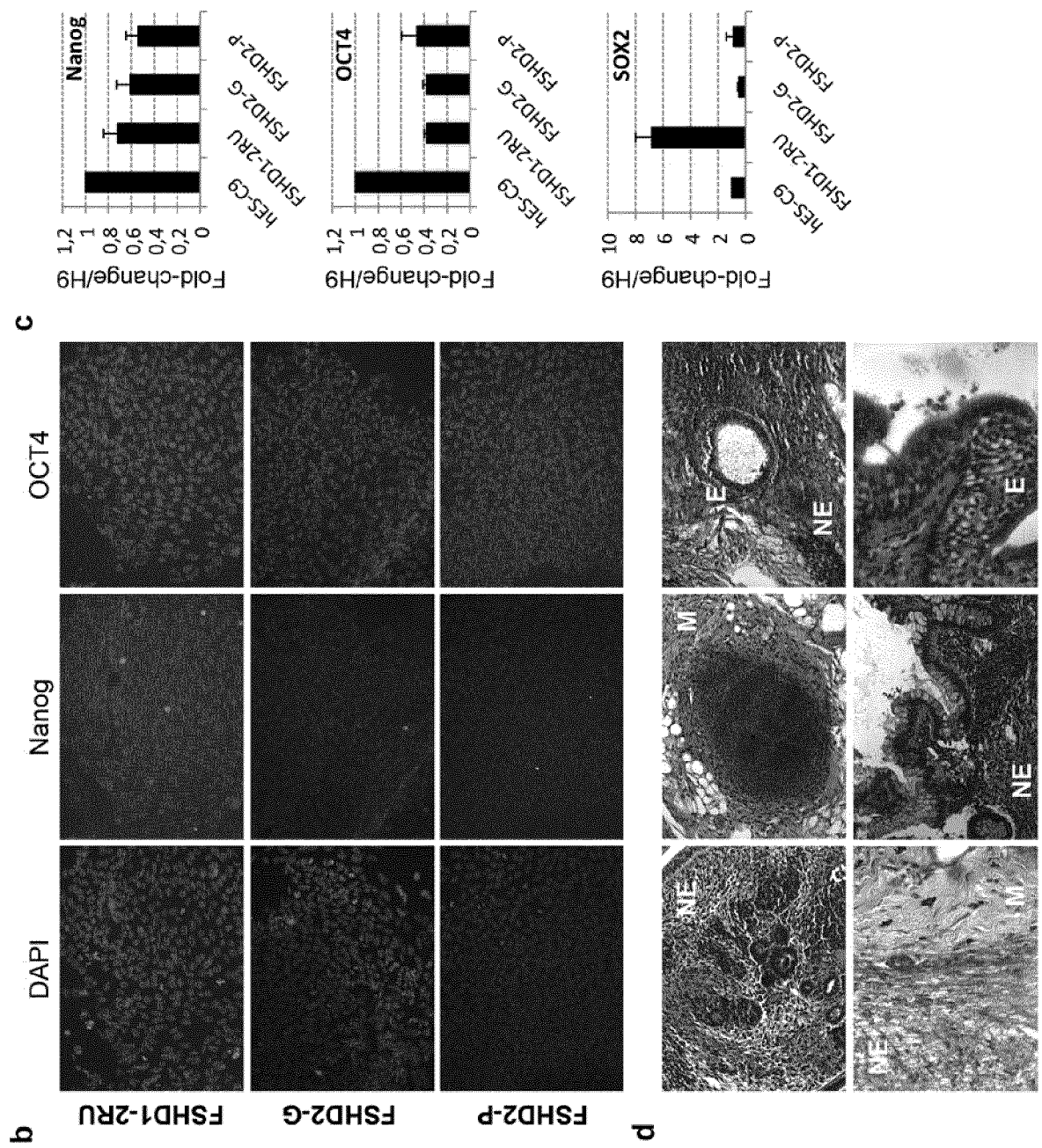

FIG. 15: Characterization of hiPSCs derived from FSHD1 or FSHD2 patients.
Human iPSCs were generated after infection of primary skin fibroblasts with a lentivirus encoding KLF4, OCT4, SOX2 and c-MYC (polycistronic STEMCCA-OKSM vector, Millipore). The two control clones (C3 and C5) were previously described (Badja et al., 2014, *Stem Cells Transl Med*). The three clones derived from FSHD patients were fully characterized using classical procedures (Marti et al., 2013), *Nature Protocols* 8, 223-253). These hiPSCs did not display any karyotype defect (a). b. Immunostaining for the Nanog and OCT4 stem cell markers. c. Reverse transcription and quantification by Real-Time PCR of Nanog, OCT4 and SOX2 in the different clones. Histogram display the mean fold-change of expression compared to the H9 hESCs. Values are normalized to the 36B4 standard gene. Error bars represent SD from three independent reactions. d. These cells are able to differentiate and form embryoid bodies when grown in suspension and form teratomas after subcutaneous injection in NOD/SCID immunodeficient mice. One to two months after injection, teratomas are collected, fixed in paraformaldehyde, paraffin embedded and stained with hematoxylin-eosin. Representative histological sections containing tissue derived from the neuroectoderm layer (NE), Mesoderm (M) or endoderm (E) are presented.

Figure 16:
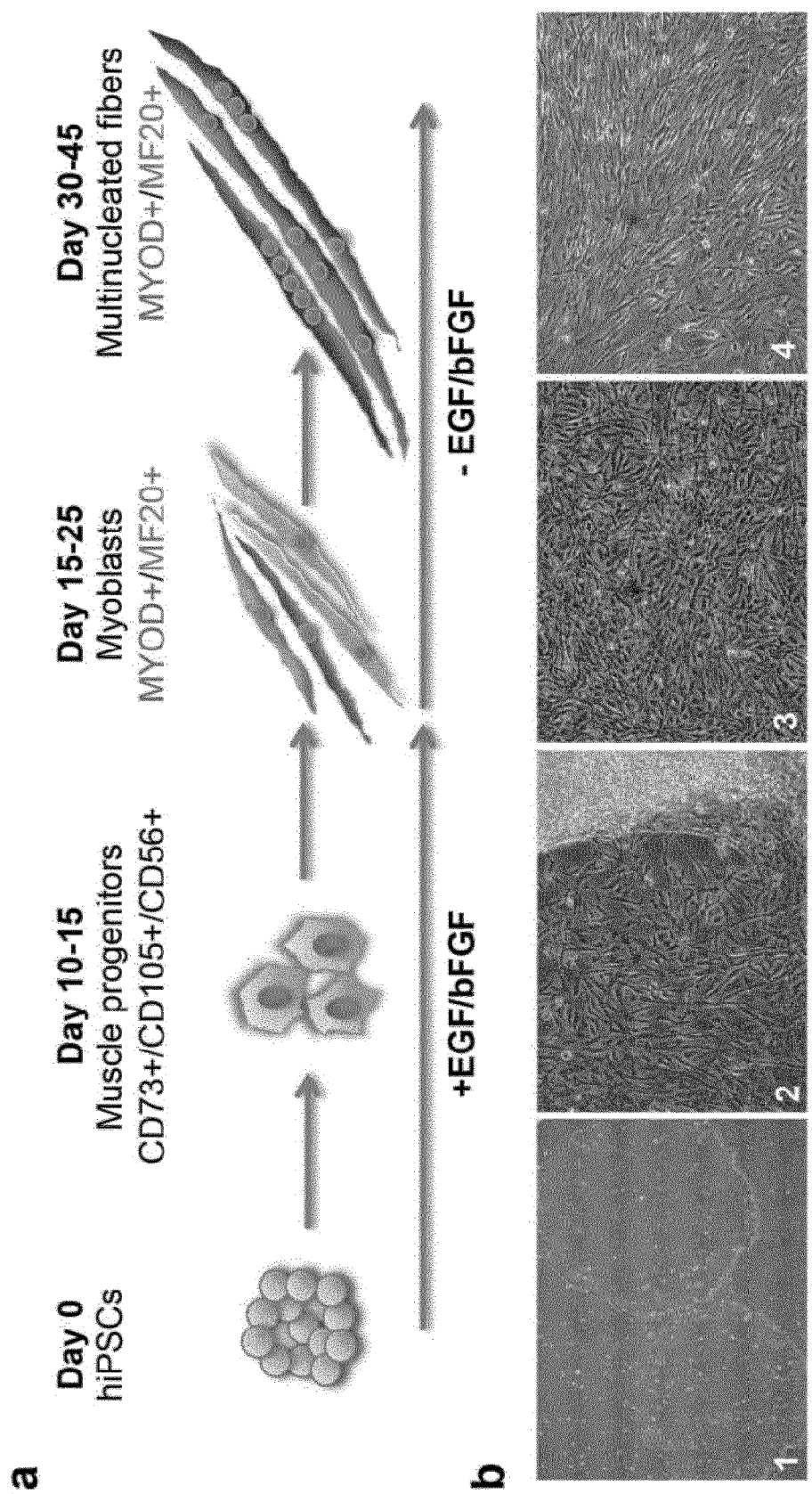
Figure 16:
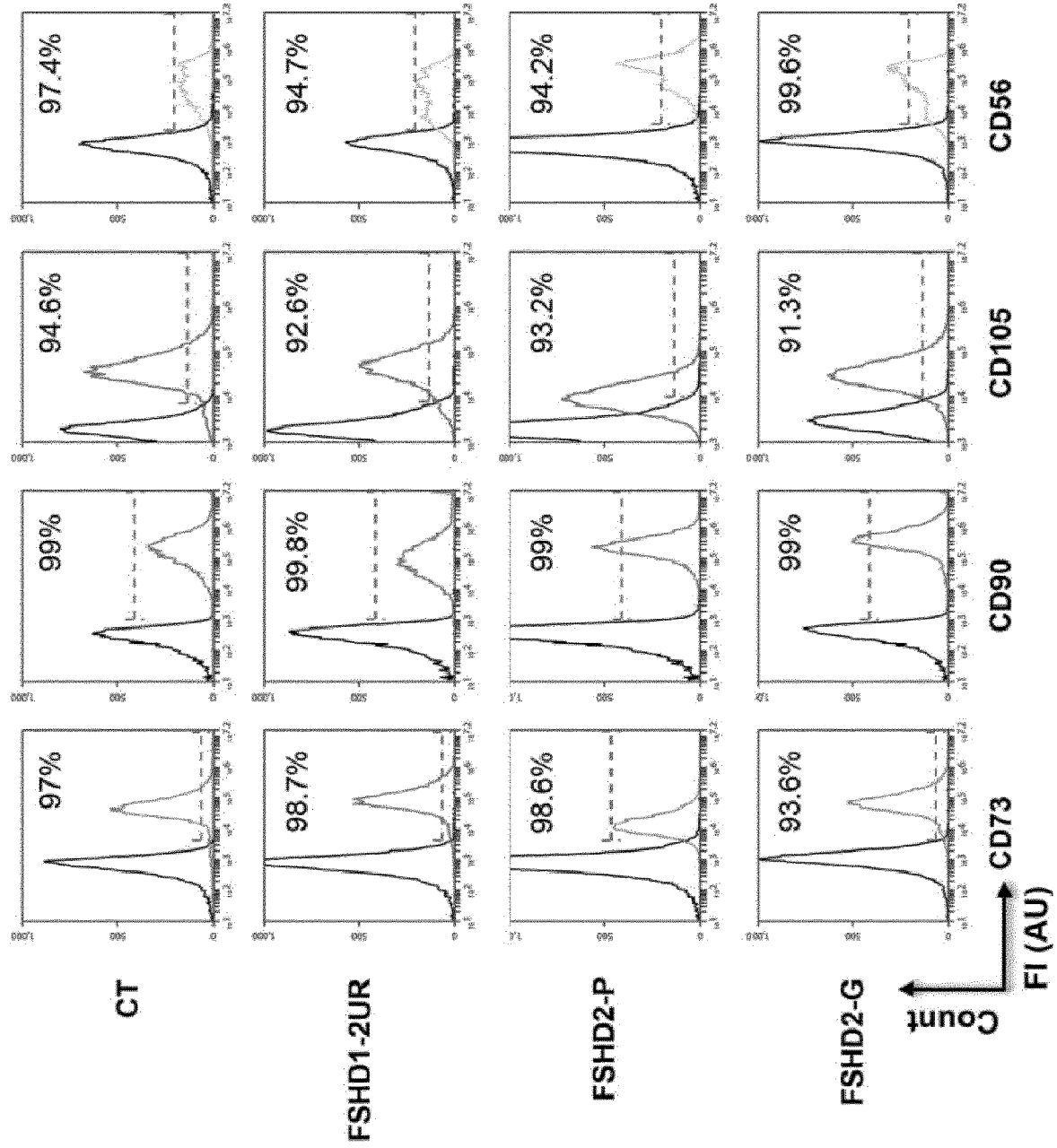

FIG. 16: Myogenic differentiation from human induced pluripotent stem cells.
a. Step 1, days 0-15; differentiation of hiPSCs into human muscle progenitors. Mature hiPSCs cultured in mTeSR on MATRIGEL-coated plates are mechanically disrupted in 30 to 50 small clumps using a 23G needle and plated onto a MATRIGEL-coated 35 mm culture dish in Differentiation Medium (DM) supplemented with 20 ng/ml bFGF, 20 ng/ml EGF. Optimal differentiation was obtained with incubation in the presence of 2% (v/v) DMSO for 16 hrs. After this overnight incubation, medium is replaced with DM+. Differentiated cells form large aggregates that can be mechanically dissociated and replated. Small cell clumps plated onto fibronectin-coated 35 mm culture dishes adhere within a few minutes. After 10-15 days, these muscle precursors can be maintained for further passages, expanded or frozen and thawed without loss of capacity. For final differentiation (step 2), cells are mechanically separated with a 23G needle and plated onto Fibronectin-coated 6 well plates in the same medium but devoid of bFGF and EGF. Medium is replaced every 2-3 days. Muscle cells develop in 5 to 10 days after plating and start to fuse and form elongated multinucleated myotubes in 30-45 days. b. Illustration of the different steps of skeletal muscle differentiation. (1) mature hiPSC colony; (2) migration of the muscle progenitors at the periphery of the cell clumps; (3) formation of a monolayer of mesenchymal progenitors (×10); (4) terminal differentiation and formation of multinucleated fibers. c. Mesenchymal progenitors were characterized by flow cytometry with antibodies against the CD73, CD90 and CD105 mesenchymal markers and CD56, a marker of muscle cell commitment. Isotypes were used to determine the background of fluorescence and set up the baseline (black line) and compensation was determined for each individual fluorochrome. (x-axis, Fluorescence Intensity (A.U); y-axis, number of cells). Percentages represent the fraction of mesenchymal stem cells positive for each marker CD73, CD90 and CD105 or the percentages of committed muscle cells positive for CD56 in the different samples, CT (control clone 3), cells from an FSHD patient (FSHD1-2UR) and two FSHD2 patients (FSHD2-G and FSHD2-P).

DETAILED DESCRIPTION OF THE INVENTION

For general methods relating to the invention, reference is made inter alia to well-known textbooks, including, e.g., "Molecular Cloning: A Laboratory Manual, 2nd Ed." (Sambrook et al., 1989), Animal Cell Culture (R. I. Freshney, ed., 1987), the series Methods in Enzymology (Academic Press), Gene Transfer Vectors for Mammalian Cells (J. M. Miller & M. P. Calos, eds., 1987); "Current Protocols in Molecular Biology and Short Protocols in Molecular Biology, 3rd Ed." (F. M. Ausubel et al., eds., 1987 & 1995); Recombinant DNA Methodology II (R. Wu ed., Academic Press 1995).

General techniques in cell culture and media uses are outlined inter alia in Large Scale Mammalian Cell Culture (Hu et al. 1997. Curr Opin Biotechnol 8: 148); Serum-free Media (K. Kitano. 1991. Biotechnology 17: 73); or Large Scale Mammalian Cell Culture (Curr Opin Biotechnol 2: 375, 1991).

For further elaboration of general techniques useful in the practice of this invention, the practitioner can refer to standard textbooks and reviews in cell biology, tissue culture, and embryology. Included are inter alia "Teratocarcinomas and embryonic stem cells: A practical approach" (E. J. Robertson, ed., IRL Press Ltd. 1987); "Guide to Techniques in Mouse Development" (P. M. Wasserman et al. eds., Academic Press 1993); "Embryonic Stem Cells: Methods and Protocols" (Kursad Turksen, ed., Humana Press, Totowa N.J., 2001); "Embryonic Stem Cell Differentiation in Vitro" (M. V. Wiles, Meth. Enzymol. 225: 900, 1993); "Properties and uses of Embryonic Stem Cells: Prospects for Application to Human Biology and Gene Therapy" (P. D. Rathjen et al., al., 1993). Differentiation of stem cells is reviewed, e.g., in Robertson. 1997. Meth Cell Biol 75: 173; Roach and McNeish. 2002. Methods Mol Biol 185: 1-16; and Pedersen. 1998. Reprod Fertil Dev 10: 31.

Any medium adapted to cultivate neuron and muscle cells may be used as a basal culture medium in the practice of the present invention for pluripotent stem cell differentiation. For example, the basal culture medium may be DMEM (Dubelcco's modified essential medium), NPBM (neuronal progenitor cell basal medium) or liquid neurobasal-A medium. Further constituents may be included in the basal medium, other than the specific factors described herein used for inducing growth and differentiation. Illustrative constituents include N2 supplement, B27 supplement, insulin, transferrin, selenium and glutamine. The basal medium may be further supplemented with serum (for example FCS) and/or antibiotics, although a serum-free and/or antibiotic-free culture medium may be more adapted in certain embodiments.

According to the invention, pluripotent stem cells are differentiated into neurons or myotubes. As used herein, the term "pluripotent stem cell" denotes a cell that has the ability to self replicate for indefinite periods and can give rise to many cell types under the right conditions, particularly, the cell types that derive from all three embryonic germ layers-mesoderm, endoderm, and ectoderm. The term "pluripotent stem cells" include mammalian, in particular human, pluripotent stem cells such as embryonic stem cells (ESC) cells or induced pluripotent stem cells. The pluripotent stem cells used in the practice of the invention are in particular human iPSCs obtained as previously described in the state of the art. The practitioner can in particular refer to Takahashi and Yamanaka; induction of pluripotent stem cells from mouse embryonic and adult fibroblast cultures by defined factors; Cell 2006; 126: 663-676 or Park et al.; Reprogramming of human somatic cells to pluripotency with defined factors; Nature 2008; 451: 141-146. iPSCs useful in the practice of the invention may be derived from a mammalian, in particular from a human subject. The cells used for obtaining iPSCs may be obtained at any stage of development, and are in particular of fetal origin, or derived from cells obtained from a young (for example a children) or adult subject. iPSCs may also be derived from any source tissue, as is well known to those skilled in the art. For example, iPSCs may be obtained from blood, skin, muscle, umbilical cord, etc. In a particular embodiment, iPSCs are generated from primary skin fibroblasts, in particular human primary skin fibroblasts. In a further particular embodiment, the source cells, in particular primary skin fibroblasts, are from a mammal, in particular an adult human. In another particular embodiment, human iPSCs are generated from source cells, in particular primary skin fibroblasts, after infection of these cells with a lentivirus encoding the four Yamanaka's factors OCT4, KLF4, SOX2 and c-MYC (OKSM). Commercial kits useful for generating iPSCs are available such as the STEMCCA-OKSM polycistronic vector from Millipore. Of course, other methods for generating iPSCs are known to a person skilled in the art, for example by using Sendai virus. Additional details on the production of iPSCs are provided in the examples. The pluripotent stem cells, in particular iPSCs, may be cultured in a medium different from the medium which is used in differentiation steps. For example, iPSCs are cultured and maintained in mTeSR, on an adapted support, for example on dishes coated with MATRIGEL or any other appropriate coating. In the practice of the present invention iPSCs may be generated from normal individuals or from individuals with any constitutive disease including development disorders, mental retardation syndrome, neurodegenerative diseases, neuromuscular pathologies, etc.

The pluripotent stem cells are then induced into neuronal or muscular progenitors. This step is carried out by first culturing them in a medium containing i) a member of the FGF family of proteins, for example bFGF, ii) EGF and iii) DMSO. In a particular embodiment, EGF and the member of the FGF family of proteins are added in the medium at a concentration of 1-100 ng/mL, in particular of 10-20 ng/mL. Furthermore, DMSO is present at a concentration of 0.5% to 5% (volume:volume) in the medium, and in particular at a concentration of 2% (v:v). This step is implemented for a duration comprised between 8 and 24 hours. Then, the culture medium is replaced by a medium containing a member of the FGF family of proteins (e.g. bFGF) and EGF, but devoid of DMSO. Culture in the medium including a member of the FGF family of proteins and EGF but devoid of DMSO may be performed for a duration comprised between 4 and 20 days, for example between 10 and 20 days, in particular between 12 and 18 days, more particularly between 14 and 16 days, the duration being in particular of 15 days. The practitioner will in particular culture the cells for a duration until the cells are at about 80-100% confluence on the cell culture support, in particular at about 80-90% confluence. This induction step (in either of the culture medium containing or not DMSO) may be implemented on a support adapted to the culture of pluripotent stem cells. For example, the culture may be feeder-dependent or feeder-free. In case of a feeder-dependent culture, the support is coated with a layer of inactive embryonic murine fibroblasts. In case of a feeder-free culture, a coating may be provided on the support, such as a coating with MATRIGEL or vitronectine. In a particular embodiment, neuronal or muscular progenitor induction is carried out as in feeder-free culture conditions, in particular on a support coated with MATRIGEL or vitronectin, more particularly with MATRIGEL.

In the next step, the induced neuronal and/or muscular progenitors are transferred in fibronectin-coated dishes (or plates, or supports, those terms being used interchangeably) onto which they are cultured in a medium containing a member of the FGF family of proteins (e.g. bFGF) and EGF. This step allows expanding the neuronal and/or muscular precursor cells (or otherwise termed progenitors). The two cell types can be distinguished based on their morphology: neuronal cells grow as a monolayer while muscle cells grow as aggregates. Alternatively, they may be distinguished by expression of cell-specific markers such as PAX6, SOX1 or Nestin for neuronal progenitors or CD56 for muscle progenitors. The induced neuronal and/or muscular progenitors may first be dissociated by implementing enzymatic or mechanical disruption before transfer to the fibronectin-coated support. In a particular embodiment, muscle progenitors aggregates are collected to separate them from neuronal progenitors that grow as a monolayer on the culture support. The muscular progenitors may then be further mechanically separated, in particular by disruption with a sterile tool such as a needle, in particular a 23G needle. The neuronal progenitors may also be separated from the culture support by an appropriate mean, such as by enzymatic disruption. Enzymatic disruption may in particular be implemented using dispase, trypsine or ACCUTASE (STREMPRO) or other enzymes known in the art. At this step of culture on a fibronectin-coated support, the cells may be expanded for several passages and maintained during at least 10 days, or at least 20 days, or at least 30 days, or at least 45 days, or more. They may also be frozen, for example at −80° C., −150° C., or even at −196° C. in liquid nitrogen, in an adapted medium, for example in the CRYOSTEMFreezing Medium (STEMGENT) or any other appropriate medium. The cells may also be used directly for neuronal or muscular differentiation according to step b) of the method of the present invention.

Step b) of the method of the invention is implemented to differentiate the expanded neuronal and muscular progenitor cells in neurons or myotubes. The neuronal and muscular progenitors may first be grown to high confluence and separated by any means known in the art, for example using an enzyme such as trypsin or ACCUTASE (STEMPRO) or by mechanical disruption, for example by disrupting cell layers with a sterile tool such as a 23G needle. The cells are then plated onto dishes that are coated with a coating which is selected depending on the desired cell lineage. Plating may be carried at a density allowing covering 10% of the dish, in particular 20%, or more. For example, cells may be plated at a density of 20-25% of the culture dish. In case neurons are desired, the cells are plated onto laminin-coated dishes after either enzymatic or mechanical disruption. In case myotubes are desired, the progenitors (in particular muscular progenitors aggregates as described above) are mechanically disrupted (such as with a needle, in particular a 23G needle) and then plated onto fibronectin-coated dishes. In case a mixture of neurons and myotubes are desired, progenitor cells are plated onto fibronectin-coated dishes after scraping and collection and dilution of cells grown as a monolayer and cells grown in suspension (i.e. aggregates of muscular progenitors). In this step, the cells are plated and cultured in a medium, for example the same base medium as the one used in the previous steps, but devoid of a member of the FGF family of proteins (e.g. bFGF) and of EGF. Step b) is implemented for at least 3 days, and the cells may be maintained in this medium one month or more with regular medium replacement, for example with a replacement every one or two days, preferably every day. In case of specialized neurons are sought, the neurons obtained according to step b) may be further differentiated using appropriate culture conditions. For example, dopaminergic neurons may be obtained by adding 50-200 ng/mL of FGF8 and 10-20 ng/mL SHH into the culture medium of the neurons obtained in step b). Dopaminergic neurons are obtained after 2 to 5 days of treatment in this medium. Other specialized neurons may be obtained, such as GABAergic neurons by culturing the neurons obtained in step b) in the presence of SHH, or by culturing them in the presence of Retinoic acid to obtain Glutamatergic neurons, or by culturing them in the presence of SAG (Smoothened Agonist), Retinoic Acid and CHIR 99021 to obtain motor neurons. In an alternative embodiment for obtaining motor neurons, neuronal progenitors and muscular progenitors as described above are both plated onto the same support for a co-culture that ultimately leads to the production of motor neurons and muscle fibers.

In a particular embodiment, the present invention relates to the co-culture and co-differentiation of skeletal muscle cells and motoneurons. In a particular variant of this embodiment, neuronal and muscle progenitors are plated in an appropriate ratio, for example in a 2:1 ratio (neuronal: muscular progenitors), on fibronectin-coated plates and maintained for 20-30 days in differentiation medium devoid of any member of the FGF family of protein and devoid of EGF. As shown in the following experimental part, in the presence of neuronal precursors, multinucleated myofibers gradually reach a high level of sarcomeric organization with Z-line structures clearly visible by light microscopy and spontaneous twitching, while neurons differentiate into motor neurons as indicated by staining for the motor neuron-specific HB9 transcription factor. Altogether, this suggests that without any member of the FGF family of protein and of EGF, or without chemical induction using factors as those described above such as SAG, retinoic acid and CHIR 99021, co-culture of neuronal and muscle progenitors induces motor neuron differentiation. In addition, the presence of motor neurons contributes to the maturation (Z-lines) and functionality (contraction) of the pluripotent stem cell-derived multinucleated myofibers together with the formation of alpha bungarotoxin-positive clusters at the surface of the Myosin Heavy Chain (MHC)-positive myotubes.

The present invention also relates to neurons and myotubes prepared according to the method described above. The present invention also relates to a composition useful for treating neurological or muscular condition, comprising the neurons or myotubes obtained as described above. The cells of the present invention may be used and transplanted directly to a patient in need thereof, or they may be first genetically modified to express or correct (increase or decrease the expression) of a protein or RNA in a neuronal or muscular tissue. Cell transplantation can be achieved using methods known in the art. Genetically modifying these cells may be useful, or even required, when the patient in need thereof whose somatic cells have been used to derive iPSCs, for example, has a disease or condition mediated by a genetic defect. Correction of this defect may be provided according to the invention. Representative diseases that may be treated using the neurons and myotubes of the present invention include neurodegenerative disorders such as for example, Alzheimer's disease, Parkinson disease, neurodevelopmental disorders such as for example, the Rett syndrome, the X-Fragile syndrome, neuromuscular diseases such as for example, Duchenne muscular dystrophy, facio-scapulo-humeral dystrophy, myotonic dystrophy, Becker myopathy, dysperlinopathies, calpainopathies, etc.

The invention also provides a method for identifying a test agent as a potential candidate for treating a neurological or muscular condition. The method comprises providing a neuron or myotube obtained according to the method described above, or a neuronal or muscular progenitor obtained as defined above, originating in particular from an individual with a neuronal or muscular condition, such as Alzheimer's disease, Parkinson disease, neurodevelopmental disorders such as for example, the Rett syndrome, the X-Fragile syndrome, neuromuscular diseases such as for example, Duchenne muscular dystrophy, facio-scapulo-humeral dystrophy, myotonic dystrophy, Becker myopathy, dysperlinopathies and calpainopathies, in particular facio-scapulo-humeral dystrophy, and testing an effect of the test compound on the neural cell or myotube. For example, if the neural cell is a dopaminergic neural cell, the effect tested is related to dopaminergic characteristics, including specific dopamine uptake.

It is further herein shown that muscle progenitor cells as derived according to the method of the invention (i.e. obtained by applying steps i, ii and iii as defined above) are able to regenerate muscle tissue in vivo after injection in a mammal. Accordingly, in one aspect, the present invention relates to a method for regenerating muscle in a subject in need thereof, comprising administering to said subject an effective amount of the muscle progenitor cell as defined above. Representative diseases that may be treated using the muscular progenitor cells of the present invention include neuromuscular diseases such as for example, Duchenne muscular dystrophy, facio-scapulo-humeral dystrophy, myotonic dystrophy, Becker myopathy, dysperlinopathies, calpainopathies, etc. In a further particular embodiment, muscle progenitor cells are derived from pluripotent stem cells originating from the subject to be treated, or from a different donor. In particular, muscle progenitor cells are derived from pluripotent stem cells originating from the subject to be treated, and which have been genetically engineered to correct any genetic deficiency that is causing muscle damage in the patient.

EXAMPLES

Experimental Procedures

Reprogramming of Human Fibroblasts to hiPSCs.

Human iPSCs were generated after infection at a Multiplicity of Infection (MOI) of 5-20 of primary skin fibroblasts with a lentivirus encoding the four Yamanaka's factors OCT4, KLF4, SOX2 and c-MYC (OKSM) (STEMCCA-OKSM polycistronic vector, Millipore).

After infection performed on 6-well plates, cells are grown in DMEM high glucose, 10% SVF-medium for five to six days. After splitting with trypsin using standard conditions, cells are grown onto 100 mm-dishes plated with Murine Embryonic Fibroblasts (MEF) treated with Mitomycin C used as feeders. Cells are grown in hES medium (KO DMEM (Life Technologies, ref 10829018) supplemented with 0.1% beta Mercaptoethanol 50 mM, 1% MEM non essential amino acids 100× (Life Technologies, ref 11140035), 20% KSR (Knock-Out Serum Replacement Medium, Life Technologies, ref 10820028), 1% penicillin-streptomycin, 1% L-Glutamine 200 mM (Life Technologies, ref 25030024) and basic FGF at 10 ng/ml final concentration. Medium is replaced every day until the emergence of hiPSCs clones. Clones are picked about 4 to 6 weeks after infection based on ES cell-like morphology. The picked clones are grown and expanded as colonies on mTeSR™ 1 medium (Stemcell technologies, cat, No. 05850) on 35 mm-dishes coated with MATRIGEL (BD Biosciences, cat, No. 354277). The hiPSCs clones generated by this method were fully characterized using classical procedures (Marti et al., Nat Protoc. 2013 February; 8(2):223-53). Expression of pluripotency markers (OCT4, NANOG, SOX2) was determined by Quantitative RT-PCR, FACS analysis and immunofluorescence staining. Genomic integrity was analyzed by karyotyping. The ability of differentiation was analyzed in vitro by formation of embryoid bodies consisting in cells of endodermal, mesodermal and ectodermal origin and in vivo by formation of teratomas after injection in immunodeficient mice.

Neuronal Differentiation (FIG. 1).

Induction of neuronal progenitors: differentiation was performed on mature hiPSCs colonies grown in mTeSR™ 1 medium on 35 mm-MATRIGEL coated plates (approximately 2×10$^6$ hiPSCs per plate). At day 1, mTeSR™ 1 medium was replaced with Differentiation Medium+(DM+) supplemented with 2% DMSO (Sigma-Aldrich, cat, No. D2438) for 8 to 24 hours. DM+ consists of: Liquid Neurobasal®-A Medium (1×), (Life Technologies, cat, No. 10888-022), 1× to 2× N2 Supplement (Life Technologies, cat, No. 17502-048); 1× to 2× B27 Supplement (Life Technologies, cat, No. 0080085-SA); 1× to 2× Insulin-Transferin-Selenium-A (ITS-A, Life Technologies, cat, No. 51300-045); Stable Glutamine (PAA, cat, No. M11-006); 20 ng/ml bFGF (PeproTech, cat, No. 100-18B) and 20 ng/ml EGF (PeproTech, cat, No. AF-100-15). Then, medium was replaced by DM+ without DMSO, and cells were grown to confluency for 10-15 days with medium replacement every one to 2 days on 35 mm MATRIGEL coated dishes.

Progenitors expansion: After 10-15 days, cells disrupted either enzymatically with ACCUTASE or mechanically with a scrapper are transferred onto 60 mm Fibronectin-coated plates (R&D Systems, cat, No. 1918-FN-02M) for further differentiation. At this step, cells can also be frozen at −80° C. in CRYOSTEM Freezing Medium (STEMGENT, cat, No. 01-0013-50). Neuronal precursors grown on 60 mm plates become highly confluent at day 25-30. At this step, cells can be dissociated mechanically or by ACCUTASE treatment (STEMPRO, cat, No. A11105-01), expanded for several passages either on 35 or 60 mm dishes depending on the number of cells required or frozen as indicated above.

Final differentiation: To induce final differentiation, highly confluent neuronal precursor cells are separated by mechanical disruption as small clumps using a G23 needle and plated on 35-60 mm Laminin-coated dishes in DM− (DM+ but without FGF and EGF). In 3 to 7 days post-plating onto Laminin, neurons grow out of the clumps and start to form connections with each others. Medium is changed every 2 days and neurons can be maintained in culture for at least one month. Higher proportions (60-90%) of Dopaminergic neurons are obtained after 2 to 5 days of treatment with 100 ng/ml FGF8 and 10 ng/ml SHH.

Neurons were characterized by RT-QPCR and IF tests in order to determine their physiological properties.

Skeletal Muscle Cell Differentiation (FIG. 2):

Induction of skeletal muscle progenitor cells: differentiation was performed on mature hiPSCS colonies grown in mTeSR™ 1 medium on 35 mm-MATRIGEL coated plates (approximately 2×10$^6$ hiPSCs per plate). At day 1, mTeSR™ 1 medium was replaced with Differentiation Medium+ (DM+) supplemented with 2% DMSO (Sigma-Aldrich, cat, No. D2438) for 8 to 24 hours. DM+ consists of: Liquid Neurobasal®-A Medium (1×), (Life Technologies, cat, No. 10888-022), 1× to 2× N2 Supplement (Life Technologies, cat, No. 17502-048); 1× to 2× B27 Supplement (Life Technologies, cat, No. 0080085-SA); 1× to 2× Insulin-Transferin-Selenium-A (ITS-A, Life Technologies, cat, No. 51300-045); Stable Glutamine (PAA, cat, No. M11-006); 10 ng/ml to 20 ng/ml bFGF (PeproTech, cat, No. 100-18B) and 10 ng/ml to 20 ng/ml EGF (PeproTech, cat, No. AF-100-15). Then, medium was replaced by DM+ without DMSO, and cells were grown to confluency for 10-15 days with medium replacement every one to 2 days on 35 mm MATRIGEL coated dishes.

Progenitors expansion: After 10-15 days, muscle progenitors cells form large aggregates that can be mechanically isolated and transferred onto 60 mm Fibronectin-coated plates (R&D Systems, cat, No. 1918-FN-02M) for further differentiation. At this step, cells can be dissociated and frozen at −80° C. in CRYOSTEMFreezing Medium (STEMGENT, cat, No. 01-0013-50). After plating, we observe a rapid change in cell morphology from round to spindle like cells positive for the NCAM myogenic marker (CD56). From day 10 to 20 skeletal muscle precursors grow on 35-60 mm Fibronectin-coated plates and become highly confluent at day 25-30. Skeletal muscle progenitors can be split and expanded for several passages either on 35 or 60 mm dishes in DM+ depending on the number of cells required or frozen as indicated above. A confluent 35 mm dish contains between 3-4×10$^5$ progenitors.

Final differentiation: From day 40 to 50 post-induction of differentiation of hiPSCs in differentiation medium, progenitors start to adopt myoblast-like morphology, orientate in parallel and fuse to form multinucleated contractile skeletal muscle cells. Spontaneous contractions are observed in 25 to 30 days after plating on fibronectin. Medium is changed every one to 2 days. Skeletal muscle cells are characterized by RT-qPCR, Flow cytometry and Immunofluorescence staining (IF).

Co-Culture of Neuronal and Skeletal Muscle Cells (FIG. 3):

Induction of neuronal and skeletal muscle progenitor cells: differentiation was performed on mature hiPSCs colonies grown in mTeSR™ 1 medium on 35 mm-MATRIGEL coated plates (approximately $2 \times 10^6$ hiPSCs per plate). At day 1, mTeSR™ 1 medium was replaced with Differentiation Medium+(DM+) supplemented with 2% DMSO (Sigma-Aldrich, cat, No. D2438) for 8 to 24 hours. DM+ consists of: Liquid Neurobasal®-A Medium (1×), (Life Technologies, cat, No. 10888-022), 1× to 2× N2 Supplement (Life Technologies, cat, No. 17502-048); 1× to 2× B27 Supplement (Life Technologies, cat, No. 0080085-SA); 1× to 2× Insulin-Transferin-Selenium-A (ITS-A, Life Technologies, cat, No. 51300-045); Stable Glutamine (PAA, cat, No. M11-006); 10 ng/ml to 20 ng/ml bFGF (PeproTech, cat, No. 100-18B) and 10 ng/ml to 20 ng/ml EGF (PeproTech, cat, No. AF-100-15). Then, medium was replaced by DM+ without DMSO, and cells were grown to confluency for 10-15 days with medium replacement every one to 2 days on 35 mm MATRIGEL coated dishes.

From day 10 to 20 post-induction, neuronal and skeletal muscle precursors can be maintained and expanded to confluence until days 25-30 on 60 mm fibronectin-coated plates after mechanical disruption for muscle precursors or enzymatic disruption for neuronal progenitors. Since differentiation medium used for muscle and neurons cells is the same, co-culture of mature multinucleated skeletal muscle cells and neurons is possible. After expansion, neuronal and muscle cell progenitors can be split and further expanded for several passages either on 35 or 60 mm dishes depending on the number of cells required. Alternatively, skeletal muscle and neuron progenitors can be plated onto 12-well Fibronectin coated dishes and feed with DM− until complete differentiation. A co-culture of mature neurons and multinucleated myotubes is obtained in 40 to 50 days after induction. Medium is changed every one to 2 days.

Coating with Poly-D-Lysine, Fibronectin, Laminin:

Fibronectin (R&D Systems, cat, No. 1918-FN-02M) and Laminin (Invitrogen, cat, No. 23017-015) are used in order to support the differentiation into neuronal and muscular progenitors, their expanding and finally induce their differentiation into mature functional cells.

Dilutions of Poly-D-Lysine, Fibronectin and Laminin at 1 mg/ml are prepared as recommended by the manufacturer and stored in small aliquots (60 µl to coat one 6-well plate or 12-well plate dishes) for several months at −20° C. For coating, a 60 µl aliquot is thawed on ice and diluted in 6 ml of DPBS 1× (10 ug/ml final concentration). One ml of diluted Poly-D-Lysine is then added per well in 6-well plates (0.5 ml per well in 12-well plates) and incubated for 1 hour at 37° C. Plates are rinsed three times in 1× DPBS and then coated with Fibronectin or Laminin, (plates can be stored for one week at 4° C.). Prior to use, plates are pre-incubated 30 minutes at 37° C. and rinsed once with 1×DPBS.

MATRIGEL coating: MATRIGEL (BD Biosciences, cat, No. 354277) coated dishes are used both for hiPSCs maintaining and differentiation. A 5 ml MATRIGEL vial is thawed at 4° C. and aliquots are prepared as recommended by the manufacturer and stored at −20° C. One aliquot is diluted in 12 ml of X-VIVO 10 (Lonza, cat, No. BE04-380Q) and used to coat 12 MATRIGEL 35 mm dish (1 ml per 35 mm dish). Aliquots are thawed on ice for 1 to 2 hours. MATRIGEL is resuspended using a 10 ml cold pipette with 12 ml of fresh X-VIVO 10 medium in a 15 ml cold conical tube on ice. One ml of MATRIGEL suspension is used per 35 mm dish. MATRIGEL-coated dishes can be stored for 2 weeks at 4° C. Before use, coated-plates are left at room temperature for 1 to 2 hours.

Immunofluorescence.

Cells are mechanically disrupted and transferred onto Laminin-coated 2-well LABTEK PERMANOX chamber slides (Thermo Scientific, cat, No. 177429) 15 days after induction. Cells are fixed in 4% paraformaldehyde for 20 min, washed with PBS, permeabilized in PBS 1×-0.1% Triton for 20 min, washed with PBS, and then incubated in blocking buffer containing 0.5% BSA for 30 min at room temperature. Incubation with primary antibodies was done overnight at 4° C. or 2 hours at room temperature. After incubation, cells were washed in PBS and incubated with ALEXA FLUOR-conjugated secondary antibodies (anti-Mouse ALEXA FLUOR 483 (1/200) or anti-Rabbit ALEXA FLUOR 555 (1/1000)) in the presence of 0.5% BSA for 1 hour. Nuclei were counterstained with DAPI. Images were acquired using an Axio Imager.Z2 (Carl Zeiss Microscopy). The following primary antibodies were used: mouse anti-Nestin (dilution 1:500, Millipore, MAB5326); Rabbit anti-NeuN (dilution 1:100, Millipore, ABN78), Rabbit anti-Tyrosine Hydroxylase (dilution 1:100, Millipore, AB152), Rabbit anti-OCT4 (dilution 1:100, Abcam, ab 19857), rabbit anti-MyoD (dilution 1:100, Santa Cruz, SC304); Rabbit anti-Desmin (dilution 1:100, Abcam, Ab15200), Mouse anti-MF20 (dilution 1:100). Vizualization was done by using either Anti-Mouse ALEXA FLUOR 483 (dilution 1:200, Ozyme 4408S) or Anti-Rabbit ALEXA FLUOR 555 (dilution 1:1000, Ozyme; 4413S).

Flow Cytometry Analysis.

Cells are treated with ACCUTASE at 37° C. during 10 minutes and rinsed with the N− medium. Cells were counted and spun down at 1000 rpm for 5 min.

For each condition, $1 \times 10^5$ cells were fixed in paraformaldehyde 4% for 20 minutes. Cells were spun down 1000 rpm for 5 mins, rinsed with BSA 0.5%, treated with Triton 0.2% for 20 mins and blocked with BSA 0.5% for 20 mins prior to the addition of the different antibodies (5 µl of antibody in 100 µl of BSA 0.5%). Samples were incubated for 30 mins. Samples were then spun down and rinsed and analyzed using an ACCURI C6 flow cytometer. Cells were analyzed on the basis of Forward Scatter (FSC-A) versus side scatter (SSC-A) for the selection of live cells and the elimination of cell aggregates or debris. Analysis of fluorescent population was limited to live cells. Unstained cells and isotype controls were used to determine the background of fluorescence and compensation was determined for individual fluorochromes. Antibodies were purchased from BD Biosciences (anti-SOX1, ref 561549; Anti-PAX6, ref 562249, Anti-NESTIN, ref 561230, anti-CD105-FITC, ref 561443; Anti-CD56-PE, ref 555516 and Anti-73-PE, ref 561014).

Quantitative and Semi-Quantitative RT-PCR and Primers.

Total RNA was extracted using TRIZOL (Invitrogen, Cat. No. 15596-026). Reverse transcription of 1 µg of total RNA was performed using the SUPERSCRIPT II kit and oligo dT following manufacturer's instructions at 42° C. for 50 minutes followed by inactivation at 70° C. for 15 minutes (Life Technologies). Primers were designed using Primer Blast and Primer3. Real-time PCR amplification was performed on a LIGHTCYCLER 480 (Roche) using the SYBR green master mix. All PCR were performed using a standardized protocol and data were analyzed with the LIGHTCYCLER 480 software version 1.5.0.39 (Roche). Fold-change was determined by absolute quantification using a standard curve and normalization to expression of the RPL19 standard gene: RPL19-F, ATC GAT CGC CAC ATG TAT CA (SEQ ID NO:1); RPL19-R, R: GCG TGC TTC CTT GGT CTT AG (SEQ ID NO:2).

Primers for neuronal progenitors are: PAX6-F, CCG GTC AAG AAA CAG AAG ACC AGA (SEQ ID NO:3); PAX6-R, CCA TTG CTA TTC TTC GGC CAG TTG (SEQ ID NO:4). SOX2-F, TCA GGA GTT GTC AAG GCA GAG AAG (SEQ ID NO:5); SOX2-R, GCC GCC GCC GAT GAT TGT TAT TAT (SEQ ID NO:6).

Primers for mature neurons are: ChAT-F, AAC CGG TTT GTC CTC TCC AC (SEQ ID NO:7); ChAT-R, TTG TAG CAG GCA CCA TAC CC (SEQ ID NO:8). DDC-F, TGT GGA AGT CAT TCT GGG GC (SEQ ID NO:9); DDC-R, CGA GAA CAG ATG GCA AAG CG (SEQ ID NO:10).

Primers for mesenchymal differentiation are: Aggrecan-F, CTG CTT CCG-AGG CAT TTC AG (SEQ ID NO:11); Aggrecan-R, CTT GGG TCA CGA TCC ACT CC (SEQ ID NO: 12). COL10A1-F, GGT ATA GCA GTA AGA GGA GAG CA (SEQ ID NO: 13); COL10A1-R, AGG ACT TCC GTA GCC TGG TTT (SEQ ID NO:14).

Primers for muscle differentiation are: PAX3-F, CAC CAG GCA TGG ATT TTC C (SEQ ID NO: 15); PAX3-R, TTG TCA GGA GTC CCA TTA CCT (SEQ ID NO: 16). PAX7-F, CCA CAG CTT CTC CAG CTA CTC (SEQ ID NO: 17); PAX7-R, GGG TTG CCC AAG ATG CTC (SEQ ID NO: 18). MYOD-F, TGC GCA ACG CCA TCC GCT A (SEQ ID NO: 19); MYOD-R, GGG CCG CTG TAG TCC ATC ATG C (SEQ ID NO: 20). MURF1-F, CTT GAC TGC CAA GCA ACT CA (SEQ ID NO: 21); MURF1-R, CAA AGC CCT GCT CTG TCT TC (SEQ ID NO: 22). MYH2-F, GGA GCT GGT GGAGGG GCC AA (SEQ ID NO: 23); MYH2-R, TGC TCC ATG GCA CCA GGA GTT T (SEQ ID NO: 24). MYH3-F, GCT TGT GGG CGG AGG TCT GG (SEQ ID NO: 25); MYH3-R, AGG GCT GGT TCT GAG CCT CGA T (SEQ ID NO: 26). MYH7-F, GGC ACG AAG GGC TTG AAT GAG GAG (SEQ ID NO: 27); MYH7-R, ATG GGG CTT TGC TGG CAC CT (SEQ ID NO: 28). MYH8-F, TCC ACC AAG AAC CCA GAG AGT GG (SEQ ID NO: 29); MYH8-R, TGG GCC TCA ATC CGC TCC TT (SEQ ID NO: 30). SCGC-F, CGA CCC GTT TCA AGA CCT TA (SEQ ID NO: 31); SCGC-R, CCT CAA TTT TCC CAG CGT GA (SEQ ID NO: 32). DSM-F, CCG CCA TCT GCG CGA GTA CC (SEQ ID NO: 33); DSM-R, TGC TCA GGG CTG GTT TCT CGG A (SEQ ID NO: 34). MGN-F, GCC TCC TGC AGT CCA GAG T (SEQ ID NO: 35); MGN-R, AGT GCA GGT TGT GGG CAT CT (SEQ ID NO: 36).

GUSB-F, CTC ATT TGG AAT TTT GCC GAT T (SEQ ID NO:37); GUSB-R, CCG AGT GAA GAT CCC CTT TTT A (SEQ ID NO:38) were used as internal standard.

Results

We developed a simple procedure to induce differentiation of human pluripotent cells (FIG. 4) into neurons (FIG. 1). The first step requires pre-differentiation and expansion of precursor cells in a defined medium on MATRIGEL-coated plates. The second step requires plating on Fibronectin then on Laminin-coated dishes for final differentiation into mature neurons (FIG. 1). Alternatively, the production of specialized neurons can be achieved in the presence of specific factors.

Following induction in the presence of DMSO, hiPS cell morphology is progressively modified (FIG. 6A,B). Immunofluorescence staining at different time points confirmed the progressive loss of the OCT4 pluripotency marker in flat spindle like cells as well as the acquisition of a neuroepithelial phenotype with expression of the Nestin neural stem cell marker indicating a switch toward the neuronal lineage (Yang et al., Cell Stem Cell. 2011; 9:517-525) as early as 4 days after induction (FIG. 6B). Expression of pluripotency markers becomes almost undetectable after 15 days (FIG. 6B). Remarkably, these neuronal progenitors self-renew, maintain their potency and can be expanded for several weeks as shown by the high rate of cells expressing Nestin, PAX6 or SOX1 at passage 1 and 6 after plating on Laminin (FIGS. 5 and 7) but the absence of expression of the BRACHYURY or SOX17 mesodermal and endodermal markers. Furthermore, this population of progenitors can be frozen and thawed without loss of capacity. This strategy is highly reproducible and similar yield were obtained on different hiPSCs clones derived from different healthy human donor dermal fibroblasts (FIG. 4).

After induction of the neuronal lineage, Nestin-positive cells (FIG. 8B) can either be maintained and expanded in differentiation medium on fibronectin-coated plates or differentiated into mature neurons on laminin-coated plates after removal of bFGF and EGF and without addition of additional factors. Final differentiation characterized by βIII-Tubulin and NeuN staining, two markers of post-mitotic neurons (FIG. 8C) and ChAT (choline acetyltransferase) (FIG. 7B) is then achieved in 5 to 7 days after plating on Laminin. In order to determine whether this protocol allows the production of specialized neurons, we also tested the differentiation toward the dopaminergic lineage by inducing mature neurons with FGF8 and SHH for 48 hrs (Carpenter et al., Methods Mol Biol. 2006; 331:153-167) (FIG. 8C). In 15 days post induction, we obtained a high enrichment in functional dopaminergic neurons expressing the tyrosine hydroxylase (TH; FIG. 8C) and DDC (FIG. 7C).

Overall, these data indicate that after plating on laminin, neuronal progenitors are differentiated into mature neurons, which can be maintained for up to 35 days without loss of membrane property as indicated by patch clamp recording. In addition, these cells can be differentiated toward specialized neurons such as dopaminergic ones in the presence of specific cytokines.

Self-renewing hESCs and hiPSCs have the potential to differentiate into any cell type thus representing an invaluable source of biological material in particular for regenerative medicine. However, in numerous cases, the use of these cells in translational medicine is hampered by the efficiency and low scale of the differentiation process.

We have described here a novel and efficient protocol for the differentiation of hiPSCs into neuronal cells. Our protocol requires no feeder layers. Furthermore, compared to other published protocols, our procedure does not necessitate embryoid bodies followed by rosette (primitive neuroepithelial cells) and neurosphere formation (Hitoshi et al., Genes Dev. 2004; 18:1806-1811; Liu et al., Nat Protoc. 2013; 8:1670-1679; Lie et al., Methods Mol Biol. 2012; 873:237-246), which might modify the purity of the cell population, drug addition, which might perturb the cellular homeostasis (Li et al., Proc Natl Acad Sci USA. 2011; 108:8299-8304; Menendez et al., Proc Natl Acad Sci USA. 2011; 108:19240-19245; Yan et al., Stem Cells Transl Med. 2013; 2:862-870; Chambers et al., Nat Biotechnol. 2009; 27:275-280; Surmacz et al., Stem Cells. 2012; 30:1875-1884) nor cell sorting limiting the quantity of differentiated cells available. Moreover, our protocol requires addition of only two cytokines at initial differentiation steps and yields large quantities of neuronal progenitors in 10-15 days, which can be maintained and regularly expanded or further differentiated.

These neuronal cells express different neuronal markers together with the $Na^+$ and $K^+$ voltage-operated channels and are able to generate and propagate action potentials. Moreover, these cells expressed different types of receptor-operated channels such as the $Cl^-$ selective GABA receptors, responsible for the main inhibitory synaptic drive in the central nervous system.

A growing number of reports describes hiPSCs-based models of constitutive disorders, opening new grounds for understanding the patho-mechanisms of these different diseases but also by allowing their use in drug discovery and potentially cell therapy. Our method can be used to produce large amount of mature neurons including dopaminergic neurons. Thus, our strategy provides a valuable tool to study neuronal differentiation pathways, synaptic and post-synaptic responses or to test pharmacological treatments opening new grounds for understanding a large number of pathologies including neurodevelopmental and neurodegenerative diseases.

In parallel, we developed a two-step procedure to induce skeletal muscle differentiation of human pluripotent cells based on the sequential use of appropriate coatings and addition or removal of cytokines. The first step requires pre-differentiation and expansion of precursor cells in a defined medium (FIG. 2). In approximately 10-15 days, large aggregates of cells form in suspension. These cell aggregates can be mechanically separated and dissociated. The second step requires plating of these clumps of cells and formation of a cell monolayer on fibronectin-coated dishes (FIG. 2). Final differentiation into mature multinucleated myotubes is induced in the presence of defined factors on fibronectin-coated plates. Our protocol requires no feeder layers and yields a high enrichment in mature mononucleated skeletal muscle cells. Pre-differentiated cells can be clonally amplified and maintained for several weeks or frozen and thawed without loss of potency or self-renewal (FIG. 2). These cells can be used for the regeneration of damaged muscle. After plating on Fibronectin, we observe a rapid change in cell morphology from round to spindle-like cells that migrate out of the cell aggregate (FIG. 9A). In order to determine their myogenic potential and the homogeneity of the population, expression of mesenchymal stem cell markers such as CD105 (Endoglin) and CD73 (5' Nucleotidase) and the NCAM (CD56) myogenic marker was analyzed on cells derived from the aggregates by flow cytometry on two different clones (FIG. 9B,C). After two weeks of differentiation, between 85 and 98% of cells express the two mesenchymal stem cell markers, CD105 and CD73 while 60 to 95% of cells are committed toward the myogenic lineage. After separation of cell aggregates, we also tested whether $CD73^+/CD105+$ might be differentiated toward other mesenchymal-derived lineages. Therefore, cells were dissociated by trypsine digestion and $5 \times 10^5$ cells were maintained for three weeks in a chondrogenic medium in the presence of BMP2. After three weeks, we observed the formation of micro pellets expressing the Aggrecan, the major proteoglycan found in cartilage and Collagen X expressed by chondrocytes (FIG. 10A). Alternatively, we also tested whether plating on other solid-coated plates such as collagen might promote muscle differentiation but did not observe further differentiation.

The myogenic program is activated by sequential expression of different skeletal muscle-specific transcription factors such as PAX3/7, MYOD, MYF5, Myogenin or MRF4 involved in the activation of satellite cells, proliferation of myoblasts or final differentiation into multinucleated myotubes. Therefore, after 15 days in culture, we measured expression of a panel of several muscle-specific markers by quantitative RT-PCR (FIG. 10B) and compared the expression pattern of hiPSCs-derived muscle cells with fetal muscle. In precursors, we were able to detect expression of PAX3 and PAX7 and MURF1 together with MYOD or myogenin. Thus, while expression level of certain myogenic markers vary between the two clones, they share common gene expression profile at the transcription level with expression of different muscle-specific genes.

For final differentiation, muscle precursors grown on fibronectin-coated plates in the absence of EGF and bFGF, can be mechanically separated, plated on fibronectin-coated dishes and maintained in this medium for 2-3 weeks (FIGS. 2; 11A). Progressively, we observed the appearance of elongated mononucleated cells that fuse to form multinucleated myotubes which express MYOD (FIG. 11B, left panel) and Desmin (FIG. 11B, right panel). We also observed expression of Myosin Heavy Chain (FIG. 11C, left and right panels), a marker of terminal muscle differentiation, in multinucleated fibers (FIG. 11C, right panel) together with Z line-like structure indicating the presence of mature fibers (FIG. 11D, left panel, phase contrast microscopy; right panel, MF20 staining). In the presence of neuronal precursors, multinucleated myofibers gradually reach a high level of sarcomeric organization with Z-line structures (FIG. 14d) and spontaneous twitching while neurons differentiate into motorneurons as indicated by staining for the motor neurons-specific HB9 transcription factor (FIG. 14c). The presence of motor neurons contributes to the maturation (Z-lines) and functionality (contraction) of the hiPSCs-derived multinucleated myofibers together with the formation of alpha bungarotoxin-positive clusters at the surface of the Myosin Heavy Chain (MHC)-positive myotubes (FIG. 14e,f).

A large number of protocols are available for the differentiation of hiPSCs in a large variety of terminally differentiated tissues but differentiation of hiPSCS or hESCs to the skeletal lineage remains difficult or requires overexpression of muscle-specific transcription factors after viral transduction or time- and labor-intensive multistep culture and cell-sorting.

Using two different lines of human iPSCS derived from healthy human donor skin fibroblasts by retroviral transduction with the OCT4, KLF4, SOX2 and c-MYC reprogramming factors, we developed a rapid and efficient protocol for the differentiation to muscle contractile cells. Thereby, mature myocytes can be efficiently generated from human hiPSCs without drug addition or introduction or induced expression of myogenic markers when cultured on appropriate coating in chemically defined conditions. One major advantage of this protocol is the possibility to generate large quantity of myogenic precursors without additional manipulation or chemical induction. Furthermore, the initial conditions of culture being the same between muscle cells and neurons, it is worth noting that this strategy can also be used for the co-culture of these two types of cells. This strategy opens new grounds for modeling a large number of pathologies of the muscle including muscular dystrophies comprising at least 40 distinct disorders but also non-genetically inherited disorders such as muscle wasting associated with ageing, cachexia, atrophy or sarcopenia that affect millions of individuals worldwide. In addition, the cells derived by the method described here would be a valuable resource for drug screening or monitoring of drug- or cell-based therapies.

In order to determine whether EGF and bFGF modify cell fate, final differentiation toward the neuronal or muscle lineage was tested in the presence of both cytokines after plating on appropriate surface, i.e. Laminin for neuronal differentiation (FIG. 12A) or fibronectin for skeletal muscle differentiation (FIG. 12C) and compared to conditions where cytokines are omitted (FIG. 12E and FIG. 12G, respectively). After plating, progenitors were maintained for 20-30 days in the presence of the two cytokines (20 ng/ml final concentration for each). We only observed a limited number of mature neurons (FIG. 12B) or elongated multi-nucleated myotubes (FIG. 12D), shown by white arrows suggesting that the removal of the two cytokines is required for final differentiation and the enrichment in mature neurons (FIG. 12F) or multinucleated myotubes (FIG. 12H).

Genetically-transmitted or acquired pathologies altering skeletal muscle affect millions of individuals worldwide. To determine whether the method of the present invention might be used for modeling neuromuscular disorders, we also applied our conditions to hiPSCs from patients suffering from Facio-Scapula-Humeral Dystrophy (FSHD1 A, OMIM 158900) (FIG. 15). This neuromuscular disorder is characterized by asymmetric and progressive weakening of muscles of the face, shoulder, scapular and pelvic girdle with a progression to the lower limbs. In most cases (95%), FSHD is linked to shortening of an array of D4Z4 macro-satellite elements at the distal 4q35 locus (Sarfarazi et al., 1992, *Am J Hum Genet* 51, 396-403; Wijmenga et al., 1992, *Nat Genet* 2, 26-30) while among the remaining 5% of patients (FSHD2), 2-3% carry a mutation in the SMCHD1 gene (Lemmers et al., 2012, *Nature Genetics* 44, 1370-1374).

Human iPSCs derived from FSHD patients were subjected to our muscular differentiation protocol, comprising culturing muscular progenitors on a support coated with fibronectin in a medium devoid of FGF and EGF. Skeletal muscle commitment was tested in hiPSCs derived from a severely affected patient carrying 2 units of the D4Z4 repeat on one of the two subtelomeric 4q35 alleles (FSHD1-2UR) and two FSHD2 patients carrying a heterozygous mutation in the SMCHD1 gene (FSHD2-G and FSHD2-P, FIG. 15) and displaying hypomethylation of the D4Z4 array (Gaillard et al., 2014, *Neurology*), an epigenetic modification often observed in FSHD. These hiPSCs show human ES-like morphology and features and did not display any karyotype defect (FIG. 15).

We obtained comparable levels of CD56-positive progenitor cells (>94%) after two weeks in differentiation medium supplemented with EGF and FGF2 for the different FSHD-derived clones and controls. These results indicate that this protocol works efficiently for cells from healthy donors or patients affected with a neuromuscular disorder (FIG. 16).

Transplantation of skeletal muscle progenitors has been considered as a possible strategy in regenerative medicine especially in the treatment of muscular dystrophies. To evaluate the capacity of our hiPSCs-derived muscle progenitors to regenerate muscle, control and FSHD1 hiPSCs-derived muscle progenitors (i.e. cells cultured in a medium containing FGF2, EGF and DMSO) were injected in a single point into the Tibialis Anterior (TA) of 7 weeks-old NOD/SCID mice 48 hrs after cryo-damage. Animals were sacrificed 1 to 3 months after injection and the presence of engrafted hiPSCs-derived myofibers was analyzed by immunofluorescence on transversal sections using antibodies specific to human Nuclei or human Spectrin (FIG. 13a, b). Transplantation of myogenic progenitors derived from controls or FSHD1-derived cells showed reactivity for anti-human Nuclei (FIG. 13a, 13b, respectively) and anti-human Spectrin (FIG. 13c, 13d, respectively). By contrast, uninjected mice showed no detectable staining for human antigens (FIG. 13e). Notably, long-term durable engraftment (3 months) showed absence of teratomas at the site of injection compared to hiPScs which usually forms teratomas in 1 to 3 months post-injection.

The invention claimed is:

1. A method for generating myotubes, comprising the steps of:
   a) culturing pluripotent stem cells in a medium containing a member of the Fibroblast Growth Factor (FGF) family of proteins, Epidermal Growth Factor (EGF) and dimethylsulfoxide (DMSO); then
   b) culturing the cells in a medium containing a member of the FGF family of proteins and EGF and devoid of DMSO; and then
   c) culturing the cells in a medium containing a member of the FGF family of proteins and EGF and devoid of DMSO on a support coated with fibronectin to obtain cells induced into muscular lineage from pluripotent stem cells;
   d) maintaining said induced cells in a culture medium comprising a member of the FGF family of proteins and EGF on a support coated with fibronectin; and
   e) culturing said induced cells in a culture medium devoid of any member of the FGF family of proteins and of EGF on a support coated with fibronectin.

2. The method according to claim 1, wherein the pluripotent stem cells are induced pluripotent cells (iPSCs) or embryonic stem (ES) cells.

3. The method according to claim 2, wherein the iPSCs are derived from a fetal, child or adult subject.

4. The method according to claim 2, wherein the iPSCs are derived from fetal, child or adult primary fibroblasts.

5. The method according to claim 1, wherein the duration of the culturing step a) is between 8 and 24 hours.

6. The method according to claim 1, wherein the duration of the culturing step b) is between 4 and 20 days.

7. The method according to claim 1, wherein the duration of step c) is of at least 10 days.

8. The method according to claim 1, wherein the cells are frozen or expanded between steps d) and e).

9. The method according to claim 1, wherein the cells are mechanically disrupted before plating them on the fibronectin-coated support of step e) to obtain myotubes.

10. The method according to claim 1, wherein the duration of step e) is of at least 3 days.

* * * * *

SEQUENCE LISTING

```
<160> NUMBER OF SEQ ID NOS: 38

<210> SEQ ID NO 1
<211> LENGTH: 20
<212> TYPE: DNA
<213> ORGANISM: artificial
<220> FEATURE:
<223> OTHER INFORMATION: primer

<400> SEQUENCE: 1
atcgatcgcc acatgtatca                                              20

<210> SEQ ID NO 2
<211> LENGTH: 20
<212> TYPE: DNA
<213> ORGANISM: artificial
<220> FEATURE:
<223> OTHER INFORMATION: primer

<400> SEQUENCE: 2
gcgtgcttcc ttggtcttag                                              20

<210> SEQ ID NO 3
<211> LENGTH: 24
```

```
<212> TYPE: DNA
<213> ORGANISM: artificial
<220> FEATURE:
<223> OTHER INFORMATION: primer

<400> SEQUENCE: 3
ccggtcaaga aacagaagac caga                                            24

<210> SEQ ID NO 4
<211> LENGTH: 24
<212> TYPE: DNA
<213> ORGANISM: artificial
<220> FEATURE:
<223> OTHER INFORMATION: primer

<400> SEQUENCE: 4
ccattgctat tcttcggcca gttg                                            24

<210> SEQ ID NO 5
<211> LENGTH: 24
<212> TYPE: DNA
<213> ORGANISM: artificial
<220> FEATURE:
<223> OTHER INFORMATION: primer

<400> SEQUENCE: 5
tcaggagttg tcaaggcaga gaag                                            24

<210> SEQ ID NO 6
<211> LENGTH: 24
<212> TYPE: DNA
<213> ORGANISM: artificial
<220> FEATURE:
<223> OTHER INFORMATION: primer

<400> SEQUENCE: 6
gccgccgccg atgattgtta ttat                                            24

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7
aaccggtttg tcctctccac                                                 20

<210> SEQ ID NO 8
<211> LENGTH: 20
<212> TYPE: DNA
<213> ORGANISM: artificial
<220> FEATURE:
<223> OTHER INFORMATION: primer

<400> SEQUENCE: 8
ttgtagcagg caccataccc                                                 20

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
```

-continued tgtggaagtc attctggggc                                            20

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
cgagaacaga tggcaaagcg                                            20

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
ctgcttccga ggcatttcag                                            20

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12
cttgggtcac gatccactcc                                            20

<210> SEQ ID NO 13
<211> LENGTH: 23
<212> TYPE: DNA
<213> ORGANISM: artificial
<220> FEATURE:
<223> OTHER INFORMATION: primer

<400> SEQUENCE: 13
ggtatagcag taagaggaga gca                                        23

<210> SEQ ID NO 14
<211> LENGTH: 21
<212> TYPE: DNA
<213> ORGANISM: artificial
<220> FEATURE:
<223> OTHER INFORMATION: primer

<400> SEQUENCE: 14
aggacttccg tagcctggtt t                                          21

<210> SEQ ID NO 15
<211> LENGTH: 19
<212> TYPE: DNA
<213> ORGANISM: artificial
<220> FEATURE:
<223> OTHER INFORMATION: primer

<400> SEQUENCE: 15
caccaggcat ggattttcc                                             19

<210> SEQ ID NO 16
<211> LENGTH: 21
<212> TYPE: DNA
<213> ORGANISM: artificial

<220> FEATURE:
<223> OTHER INFORMATION: primer

<400> SEQUENCE: 16
ttgtcaggag tcccattacc t                                              21

<210> SEQ ID NO 17
<211> LENGTH: 21
<212> TYPE: DNA
<213> ORGANISM: artificial
<220> FEATURE:
<223> OTHER INFORMATION: primer

<400> SEQUENCE: 17
ccacagcttc tccagctact c                                              21

<210> SEQ ID NO 18
<211> LENGTH: 18
<212> TYPE: DNA
<213> ORGANISM: artificial
<220> FEATURE:
<223> OTHER INFORMATION: primer

<400> SEQUENCE: 18
gggttgccca agatgctc                                                  18

<210> SEQ ID NO 19
<211> LENGTH: 19
<212> TYPE: DNA
<213> ORGANISM: artificial
<220> FEATURE:
<223> OTHER INFORMATION: primer

<400> SEQUENCE: 19
tgcgcaacgc catccgcta                                                 19

<210> SEQ ID NO 20
<211> LENGTH: 22
<212> TYPE: DNA
<213> ORGANISM: artificial
<220> FEATURE:
<223> OTHER INFORMATION: primer

<400> SEQUENCE: 20
gggccgctgt agtccatcat gc                                             22

<210> SEQ ID NO 21
<211> LENGTH: 20
<212> TYPE: DNA
<213> ORGANISM: artificial
<220> FEATURE:
<223> OTHER INFORMATION: primer

<400> SEQUENCE: 21
cttgactgcc aagcaactca                                                20

<210> SEQ ID NO 22
<211> LENGTH: 20
<212> TYPE: DNA
<213> ORGANISM: artificial
<220> FEATURE:
<223> OTHER INFORMATION: primer

<400> SEQUENCE: 22
caaagccctg ctctgtcttc                                                20

```
<210> SEQ ID NO 23
<211> LENGTH: 20
<212> TYPE: DNA
<213> ORGANISM: artificial
<220> FEATURE:
<223> OTHER INFORMATION: primer

<400> SEQUENCE: 23
ggagctggtg gagggggccaa                                                  20

<210> SEQ ID NO 24
<211> LENGTH: 22
<212> TYPE: DNA
<213> ORGANISM: artificial
<220> FEATURE:
<223> OTHER INFORMATION: primer

<400> SEQUENCE: 24
tgctccatgg caccaggagt tt                                                22

<210> SEQ ID NO 25
<211> LENGTH: 20
<212> TYPE: DNA
<213> ORGANISM: artificial
<220> FEATURE:
<223> OTHER INFORMATION: primer

<400> SEQUENCE: 25
gcttgtgggc ggaggtctgg                                                   20

<210> SEQ ID NO 26
<211> LENGTH: 22
<212> TYPE: DNA
<213> ORGANISM: artificial
<220> FEATURE:
<223> OTHER INFORMATION: primer

<400> SEQUENCE: 26
agggctggtt ctgagcctcg at                                                22

<210> SEQ ID NO 27
<211> LENGTH: 24
<212> TYPE: DNA
<213> ORGANISM: artificial
<220> FEATURE:
<223> OTHER INFORMATION: primer

<400> SEQUENCE: 27
ggcacgaagg gcttgaatga ggag                                              24

<210> SEQ ID NO 28
<211> LENGTH: 20
<212> TYPE: DNA
<213> ORGANISM: artificial
<220> FEATURE:
<223> OTHER INFORMATION: primer

<400> SEQUENCE: 28
atggggcttt gctggcacct                                                   20

<210> SEQ ID NO 29
<211> LENGTH: 23
<212> TYPE: DNA
<213> ORGANISM: artificial
<220> FEATURE:
<223> OTHER INFORMATION: primer
```

```
<400> SEQUENCE: 29
tccaccaaga acccagagag tgg                                              23

<210> SEQ ID NO 30
<211> LENGTH: 20
<212> TYPE: DNA
<213> ORGANISM: artificial
<220> FEATURE:
<223> OTHER INFORMATION: primer

<400> SEQUENCE: 30
tgggcctcaa tccgctcctt                                                  20

<210> SEQ ID NO 31
<211> LENGTH: 20
<212> TYPE: DNA
<213> ORGANISM: artificial
<220> FEATURE:
<223> OTHER INFORMATION: primer

<400> SEQUENCE: 31
cgacccgttt caagacctta                                                  20

<210> SEQ ID NO 32
<211> LENGTH: 20
<212> TYPE: DNA
<213> ORGANISM: artificial
<220> FEATURE:
<223> OTHER INFORMATION: primer

<400> SEQUENCE: 32
cctcaatttt cccagcgtga                                                  20

<210> SEQ ID NO 33
<211> LENGTH: 20
<212> TYPE: DNA
<213> ORGANISM: artificial
<220> FEATURE:
<223> OTHER INFORMATION: primer

<400> SEQUENCE: 33
ccgccatctg cgcgagtacc                                                  20

<210> SEQ ID NO 34
<211> LENGTH: 22
<212> TYPE: DNA
<213> ORGANISM: artificial
<220> FEATURE:
<223> OTHER INFORMATION: primer

<400> SEQUENCE: 34
tgctcagggc tggtttctcg ga                                               22

<210> SEQ ID NO 35
<211> LENGTH: 19
<212> TYPE: DNA
<213> ORGANISM: artificial
<220> FEATURE:
<223> OTHER INFORMATION: primer

<400> SEQUENCE: 35
gcctcctgca gtccagagt                                                   19

<210> SEQ ID NO 36
```

```
<211> LENGTH: 20
<212> TYPE: DNA
<213> ORGANISM: artificial
<220> FEATURE:
<223> OTHER INFORMATION: primer

<400> SEQUENCE: 36
agtgcaggtt gtgggcatct                                               20

<210> SEQ ID NO 37
<211> LENGTH: 22
<212> TYPE: DNA
<213> ORGANISM: artificial
<220> FEATURE:
<223> OTHER INFORMATION: primer

<400> SEQUENCE: 37
ctcatttgga attttgccga tt                                            22

<210> SEQ ID NO 38
<211> LENGTH: 22
<212> TYPE: DNA
<213> ORGANISM: artificial
<220> FEATURE:
<223> OTHER INFORMATION: primer

<400> SEQUENCE: 38
ccgagtgaag atcccctttt ta                                            22
```